United States Patent
Miyawaki et al.

(10) Patent No.: US 9,957,308 B2
(45) Date of Patent: May 1, 2018

(54) METHOD FOR DETECTING BILIRUBIN USING A FLUORESCENT PROTEIN

(71) Applicant: RIKEN, Wako-shi, Saitama (JP)

(72) Inventors: Atsushi Miyawaki, Wako (JP); Akiko Kumagai, Wako (JP)

(73) Assignee: RIKEN, Wako-Shi, Saitama (JP)

(*) Notice: Subject to any disclaimer, the term of this patent is extended or adjusted under 35 U.S.C. 154(b) by 0 days. days.

(21) Appl. No.: 14/771,060

(22) PCT Filed: Feb. 28, 2014

(86) PCT No.: PCT/JP2014/055160
§ 371 (c)(1),
(2) Date: Aug. 27, 2015

(87) PCT Pub. No.: WO2014/133158
PCT Pub. Date: Sep. 4, 2014

(65) Prior Publication Data
US 2016/0009771 A1    Jan. 14, 2016

(30) Foreign Application Priority Data

Feb. 28, 2013  (JP) ................... 2013-040097

(51) Int. Cl.
| | | |
|---|---|---|
| *G01N 33/50* | (2006.01) | |
| *G01N 33/52* | (2006.01) | |
| *C07K 14/46* | (2006.01) | |
| *G01N 33/72* | (2006.01) | |
| *C07K 14/00* | (2006.01) | |
| *C12Q 1/68* | (2018.01) | |

(52) U.S. Cl.
CPC ........... *C07K 14/461* (2013.01); *C07K 14/00* (2013.01); *C12Q 1/6816* (2013.01); *G01N 33/72* (2013.01); *C07K 2319/60* (2013.01); *G01N 2800/085* (2013.01); *G01N 2800/22* (2013.01)

(58) Field of Classification Search
None
See application file for complete search history.

(56) References Cited

U.S. PATENT DOCUMENTS

2016/0146838 A1* 5/2016 Brisard ............ G01N 33/6893
436/501

FOREIGN PATENT DOCUMENTS

| JP | 2007-254371 A | 10/2007 | |
| JP | 2008-141988 A | 6/2008 | |
| WO | WO 2013032953 A2 * | 3/2013 | ........... G01N 33/533 |

OTHER PUBLICATIONS

Honda, Masao, et al., "Unagi Kinniku no Ryokushoku Keiko Tanpakushitsu", 2004 Nen (Helsei 16 Nen) Do Abstracts for the Annual Meeting of the Japanese Society of Fisheries Science, Mar. 31, 2004 (Mar. 31, 2004), pp. 203, 1101.
Hayashi, S., et al., "A novel fluorescent protein purified from eel muscle", Fisheries Science, 2009, vol. 75, pp. 1461-1469.
Kumagai, A., et al., "A Bilirubin-Inducible Fluorescent Protein from Eel Muscle", Cell, 2013, vol. 153, pp. 1602-1611.

* cited by examiner

*Primary Examiner* — David Steadman
(74) *Attorney, Agent, or Firm* — Lucas & Mercanti, LLP

(57) ABSTRACT

In order to provide a novel fluorescent protein and use thereof, the polypeptide according to the present invention has fluorescent properties in the presence of bilirubin and includes (1) the amino acid sequence of SEQ ID NO: 1, (2) an amino acid sequence having, for example, substitution of 1 to 21 amine acids in the amino acid sequence of SEQ ID NO: 1, (3) an amino acid sequence having 85% or more sequence identity to the amino acid sequence of SEQ ID NO: 1, or (4) the amino acid sequence encoded by a polynucleotide that hybridizes with a polynucleotide consisting of a sequence complementary to the polynucleotide encoding the polypeptide according to the amino acid sequence in (1) under a stringent condition.

10 Claims, 11 Drawing Sheets

METHOD FOR DETECTING BILIRUBIN USING A FLUORESCENT PROTEIN

CROSS-REFERENCE TO RELATED APPLICATIONS

This application is a 371 of PCT/JP2014/055160, filed Feb. 28, 2014, which claims the benefit of Japanese Patent Application No. 2013-040097, filed Feb. 28, 2013.

TECHNICAL FIELD

The present invention relates to a novel polypeptide capable of being isolated from vertebrates and having fluorescent properties and to use thereof.

BACKGROUND ART

Fluorescent proteins, such as green fluorescent protein (GFP), are indispensable as a tool for visualizing cells, tissue, biological individuals, and so on.

Most of fluorescent proteins have been isolated from invertebrates such as coral, sea anemones, and arthropods. However, for example, Non Patent Literatures 1 and 2 and Patent Literatures 1 and 2 report that a vertebrate, Japanese eel (*Anguilla japonica*), has a fluorescent protein.

CITATION LIST

Patent Literature

Patent Literature 1: JP Patent Publication (Kokai) No. 2001-254371 A (Date of publication: Oct. 4, 2007)
Patent Literature 2: JP Patent Publication (Kokai) No. 2008-141988 A (Date of publication: Jun. 26, 2008)

Non Patent Literature

Non Patent Literature 1: Masao HONDA, Jinsuke Miyuki IMAMURA, Seiichi HAYASHI: Abstracts of the Fiscal Year Heisei 16 meeting of the Japanese Society of Fisheries Science (Apr. 2, 2004, p. 203, 1101)
Non Patent Literature 2: Hayashi et al., Fisheries Science, 75, 1461-4469, 2009

SUMMARY OF INVENTION

Technical Problem

There is a possibility that fluorescent proteins derived from vertebrates have characteristics different from those of fluorescent proteins derived from invertebrates. Accordingly, the study of isolating fluorescent proteins derived from vertebrates is very interesting.

However, although investigating for a very long time since the publication of Patent Literatures 1 and 2 and Non Patent Literatures 1 and 2, the full length of any fluorescent protein derived from a vertebrate and the gene encoding the fluorescent protein have not been isolated yet.

The present invention has been made for solving the above-described problems, and it is an object thereof to provide a novel fluorescent protein that can be isolated from a vertebrate and use of the fluorescent protein.

Solution to Problem

In order to solve the above-mentioned problems, the present invention encompasses any one of the following aspects:

1) A polypeptide having fluorescent properties in the presence of bilirubin, represented by any of the following (1) to (4): (1) a polypeptide including the amino acid sequence of SEQ ID NO: 1; (2) a polypeptide including an amino acid sequence having substitution, deletion, insertion, and/or addition of 1 to 21 amino acids in the amino acid sequence of SEQ ID NO: 1; (3) a polypeptide having 85% or more sequence identity to the amino acid sequence of SEQ ID 1; and (4) a polypeptide including the amino acid sequence encoded by a polynucleotide that hybridizes with a polynucleotide consisting of a sequence complementary to the polynucleotide encoding the polypeptide according to (1) under a stringent condition; and 2) A polynucleotide according to any of the following (1) to (4): (1) a polynucleotide encoding a polypeptide including the amino acid sequence of SEQ ID NO: 1; (2) a polynucleotide encoding a polypeptide including an amino acid sequence having substitution, deletion, insertion, and/or addition of 1 to 21 amino acids in the amino acid sequence of SEQ ID NO: 1 and having fluorescent properties in the presence of bilirubin; (3) a polynucleotide encoding a polypeptide having 85% or more sequence identity to the amino acid sequence of SEQ ID NO: 1 and having fluorescent properties in the presence of bilirubin; and (4) a polynucleotide hybridizing with a polynucleotide consisting of a sequence complementary to the polynucleotide according to (1) under a stringent condition and encoding a polypeptide having fluorescent properties in the presence of bilirubin.

Advantageous Effects of Invention

The present invention has an effect of providing a fluorescent protein useful in, for example, the field of molecular biology and use of the fluorescent protein.

BRIEF DESCRIPTION OF DRAWINGS

FIG. 9 is a graph showing a correlation between the concentration of bilirubin and the fluorescence intensity ratio of wild-type UnaG protein, or A12ES80N mutated UnaG protein to mCherry protein in Example of the present invention.

DESCRIPTION OF EMBODIMENTS

Figure 1:
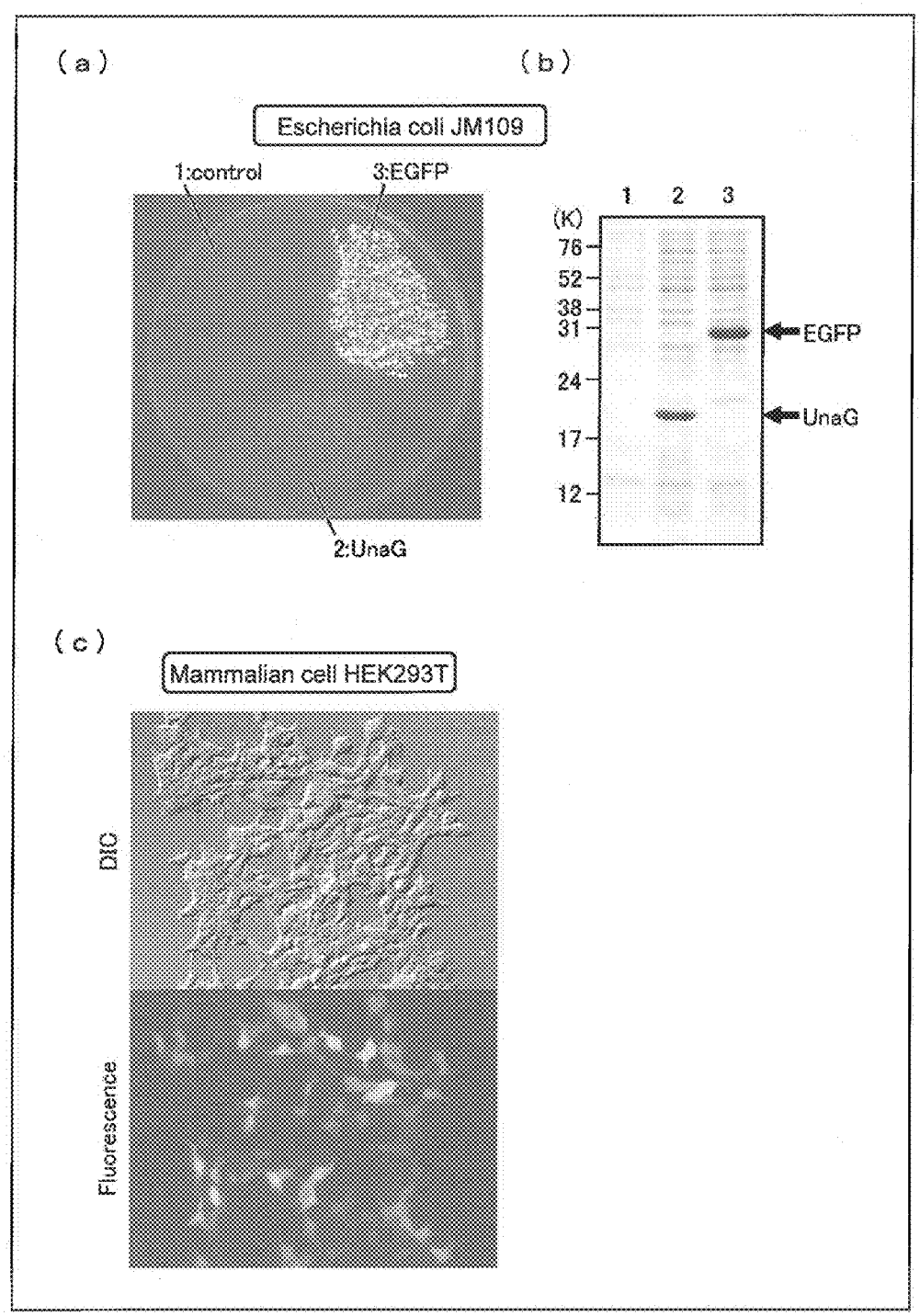
FIG. 1 includes diagrams showing expression of recombinant UnaG protein in *Escherichia coli* and mammalian cells in Example of the present invention: the diagram (a) shows the observation results of *Escherichia coli* (2) expressing recombinant UnaG protein by irradiation with blue light with UV transilluminator, where the diagram at the upper left shows *Escherichia coli* cells (1) transfected with vector pRSET as a control, and the upper right is a diagram showing *Escherichia coli* cells (3) expressing EGFP; the diagram (b) shows electrophoretic gels of SDS-PAGE electrophoresis of cell extracts from *Escherichia coli* (1) to (3) shown in diagram (a), stained by CBB staining; and the diagram (c) shows the observation results of mammalian cell HEK293T expressing recombinant UnaG protein under a fluorescence microscope, where the upper is a differential interference image, and the lower is a fluorescence image.

An embodiment of the present invention will now be described in detail.

[Definition of Terms, Etc.]

Throughout the specification, the term "polynucleotide" can also be referred to as "nucleic acid" or "nucleic acid molecule" and refers to a polymer of nucleotides. The term "nucleotide sequence" can also be referred to as "nucleic acid sequence" and refers to a sequence of deoxyribonucleotides sir ribonucleotides, unless specified otherwise. The polynucleotide may be a single-stranded or double-stranded structure, and a single-stranded polynucleotide may be a sense strand or an anti-sense strand.

Throughout the specification, the term "polypeptide" can also be referred to as "protein".

Throughout the specification, the term "eel" is intended to include fishes belonging to Ariguillidae Anguilla, such as Japanese eel, European eel, American eel, and giant mottled eel.

Throughout the specification, the term "A and/or B" is a concept including both "A and B" and "A or B" and can also be referred to as "at least one of A and B".

Throughout the specification, the term "bilirubin" refers to degradation products of a component of hemoglobin, heme. A preferred aspect of bilirubin in the present invention is unconjugated bilirubin. Unconjugated bilirubin is also referred to as indirect bilirubin.

[1. Polypeptide Having Fluorescent Properties]

The polypeptide according to the present invention is a polypeptide having fluorescent properties in the presence of bilirubin (hereinafter, referred to as "fluorescent polypeptide") and represented by any of the following (1) to (4):

(1) Fluorescent polypeptides including the amino acid sequence of SEQ ID NO: 1;

(2) Fluorescent polypeptides including an amino acid sequence having substitution, deletion, insertion, and/or addition of 1 to 21 amino acids in the amino acid sequence of SEQ ID NO: 1, where the number of amino acids substituted, deleted, inserted, and/or added is preferably 1 to 21, more preferably 1 to 14, more preferably 1 to 7, and most preferably 1 to 5 or 6;

(3) Fluorescent polypeptides having 85% or more sequence identity to the amino acid sequence of SEQ ID NO: 1, where the sequence identity is preferably 90% or more, more preferably 95% or more, and most preferably 96% or more, 97% or more, 98% or more, or 99% or more; and (4) Fluorescent polypeptides including the amino acid sequence encoded by a polynucleotide that hybridizes with a polynucleotide consisting of a sequence complemen to the polynucleotide encoding a fluorescent polypeptide according to (1) under a stringent condition, where the stringent condition will be described below in the paragraph of polynucleotide according to the present invention.

The fluorescent polypeptide according to the present invention does not have fluorescent properties under an environment losing the interaction with bilirubin, such as the absence of bilirubin. Such unprecedented fluorescent properties are probably one of causes of difficulty in isolation of the polypeptide.

The fluorescent polypeptide may be any polypeptide composed of amino acids joined by peptide bonds, but is not limited thereto. For example, the fluorescent polypeptide may contain a structure other than polypeptides. Non-limited examples of the structure other than the polypeptide include carbohydrate chains and isoprenoid groups. The fluorescent polypeptide has a structure serving as a site binding to bilirubin.

The fluorescent polypeptide according to the present invention may be isolated from a natural source or may be chemically synthesized. More specifically, purified natural products, chemically synthesized products, and translation products produced by recombinant technology from prokaryotic or eukaryotic hosts (e.g., bacterial cells, yeast cells, higher plant cells, insect cells, or mammalian cells) are encompassed in the category of the polypeptide. An example of the fluorescent polypeptide according to the present invention is that derived from eel, more specifically, derived from Japanese eel. Although the fluorescent polypeptide including the amino acid sequence of SEQ ID NO: 1

(referred to as UnaG) is originally isolated from Japanese eel, the origin of the fluorescent polypeptide is not limited thereto.

The fluorescent polypeptide according to the present invention is a group of polypeptides possessing a common characteristic of emitting fluorescence having a prescribed wavelength by irradiation with excitation light in the presence of bilirubin (a form of being bound to bilirubin), but not emitting fluorescence by irradiation with the same excitation light in the absence of bilirubin. The fluorescent polypeptide may be any fluorescent polypeptide satisfying the characteristic of emitting fluorescence in the presence of a ligand and may be a polypeptide (including a mutated fluorescent polypeptide) that emits fluorescence in the further presence of another compound (e.g., bilirubin analogous compound) in addition to bilirubin.

The fluorescent polypeptide according to the present invention is preferred to further have fluorescent properties equivalent to those of UnaG in some cases. Here, having equivalent fluorescent properties refers to having substantially the same excitation and fluorescence wavelengths.

Main fluorescent properties of UnaG are as follows:
Maximum excitation wavelength (nm): 498 to 499,
Maximum fluorescence wavelength (nm): 525 to 530 (green),
Molar extinction coefficient ($M^{-1}cm^{-1}$): 50000 to 78000,
Quantum yield (%): 50 to 54, and
Fluorescence lifetime (nanosecond): 2.2.

Having an excitation wavelength substantially the same as that in UnaG means, for example, that the maximum excitation wavelength is within a range of 480 to 520 nm, or a range of 490 to 510 nm, or a range of 494 to 504 nm.

Having a fluorescence wavelength substantially the same as that in UnaG means, for example, that the maximum fluorescence wavelength is within a range of 507 to 547 nm, or a range of 517 to 537 nm, or a range of 522 to 532 nm.

In the fluorescent polypeptides shown in the above-mentioned (1) to (4), those defined in (2) to (4) can be comprehended as variants when the polypeptide defined (1) is used as a reference. For example, those skilled in the art can introduce a mutation by an arbitrary method in order to enhance at least one fluorescent property selected from fluorescence intensity, fluorescence rate, and stability of fluorescence. Here, the fluorescence intensity is a digitized index of intensity of light emitting fluorescence and refers to the brightness of fluorescence proportional to light absorption efficiency (i.e., extinction coefficient) and conversion efficiency (i.e., quantum yield) between excitation light and fluorescence. The fluorescence rate refers to the digitized value of the speed for in reaching a prescribed fluorescence intensity from the reception of excitation light. The stability of fluorescence refers to a property possessed by the fluorescent polypeptide, judged from the time maintaining a prescribed fluorescence intensity as an index. That is, a lower degree of decay in fluorescence within fixed time refers to higher stability of fluorescence.

In the fluorescent polypeptides defined in (1), nine amino acids, 12th, 57th, 61st, 77th, 80th, 81st, 112th, 132nd, and 134th amino acids, in SEQ ID NO: 1 are particularly involved in the capacity of binding to bilirubin. Accordingly, in order to prepare a variant having a change in capacity of binding to bilirubin, variation (substitution, deletion, insertion, and/or addition, preferably substitution by another amino acid) is preferably introduced into at least one of these nine amino acids. In contrast, in order to prepare a variant maintaining substantially the same capacity of binding to bilirubin, variation is preferably introduced into an amino acid or amino acids other than the above-mentioned nine amino acids. For example, variation (preferably substitution by another amino acid) of at least one amino acid selected from 82nd to 85th, more preferably 82nd and 84th, amino acids of SEQ ID NO: 1 can provide a fluorescent polypeptide substantially maintaining the fluorescent properties and having improved mutual dispersibility of molecules (also see Examples).

In particular, in order to reduce the capacity of binding to bilirubin while maintaining the fluorescent properties of the polypeptide according to the present invention, in the fluorescent polypeptides defined in (1), variation is preferably introduced into at least one of four amino acids, 12th, 57th, 61st, and 80th amino acids, in SEQ ID NO: 1, more preferably at least one of 12th, 61st, and 80th amino acids, and most preferably 12th and 80th amino acids. These amino acids are each involved in the capacity of binding to bilirubin through a hydrogen bond with bilirubin. For example, variation (preferably substitution by another amino acid) into 12th and 80th amino acids can provide a fluorescent polypeptide substantially maintaining the fluorescent properties and having reduced capacity of binding to bilirubin compared to UnaG (also see Examples).

The fluorescent polypeptide having reduced capacity of binding to bilirubin compared to UnaG can be suitably used in, for example, detection of bilirubin in a subject.

A method for detecting bilirubin in a subject is described in detail below in paragraph [6. Detection of bilirubin subject].

The capacity of binding to bilirubin can be evaluated through calculation of dissociation constant (Kd) by curve-fitting of correlation between the amount of bilirubin and the fluorescence intensity of UnaG protein. In one instance, "reduced capacity of binding to bilirubin compared to UnaG" means that the dissociation constant, Kd, is larger than that of UnaG.

Incidentally, UnaG has a dissociation constant, Kd, of 98 pM.

In one instance, a fluorescent polypeptide having reduced capacity of binding to bilirubin compared to UnaG has a dissociation constant Kd 1000 times or more, preferably 100 times or more and more preferably 15 to 20 times or more that of UnaG.

A dissociation constant Kd suitable for detection of bilirubin is preferably 0.1 nM or more and 100 nM or less, more preferably 0.1 nM or more and 10 nM or less, and most preferably 0.1 nM or more and 2 nM or less.

The dissociation constant can be calculated by a known method, for example, by the following computation expression:

$$Y=[K_d+B_t+P_t-\{(K_d+B_t+P_t)^{1/2}\}]/(2\times P_t)$$

where Y represents the degree of binding of bilirubin (fluorescence intensity); $K_d$ represents the dissociation constant; $B_t$ represents the concentration of bilirubin; and $P_t$ represents the concentration (5 nM) of apo UnaG protein.

In the fluorescent polypeptides defined in (2) to (4), variation may be artificially introduced into the polynucleotide encoding a fluorescent polypeptide defined in (1) by site-directed mutagenesis, such as a Kunkel method (Kunkel, et al., (1985): Proc. Natl. Acad. Sci. USA, Vol. 82, p. 488). Examples of such a fluorescent polypeptide include those including an amino acid sequence of SEQ ID NO: 5 or SEQ ID NO: 29 and also include those derived from naturally occurring variant polypeptides. Other examples of this fluorescent polypeptide include those including the amino acid sequence of SEQ ID NO: 3.

[3. Polynucleotide Encoding Fluorescent Polypeptide]

The polynucleotide according to the present invention encodes any of the above-mentioned fluorescent polypeptides. Specifically, this polynucleotide is any of the polynucleotides according to the following (1) to (4):

(1) a polynucleotide encoding a polypeptide including the amino acid sequence of SEQ ID NO: 1;

(2) a polynucleotide encoding a polypeptide including an amino acid sequence having substitution, deletion, insertion, and/or addition of 1 to 21 amino acids in the amino acid sequence of SEQ ID NO: 1 and having fluorescent properties in the presence of bilirubin, where the number of amino acids substituted, deleted, inserted, and/or added is preferably 1 to 21, more preferably 1 to 14, more preferably 1 to 7, and most preferably 1 to 5 or 6;

(3) a polynucleotide encoding a polypeptide having 85% or more sequence identity to the amino acid sequence of SEQ NO:1 and having fluorescent properties in the presence of bilirubin, where the sequence identity to the amino acid sequence is preferably 90% or more, more preferably 95% or more, and most preferably 96% or more, 97% or more, 98% or more, or 99% or more. For example, a mutant gene derived from eel or a homologouS gene derived from an organism other than eel is encompassed in this category; and (4) a polynucleotide hybridizing with a polynucleotide consisting of a sequence complementary to the polynucleotide according to (1) under a stringent condition and encoding a polypeptide having fluorescent properties in the presence of bilirubin. Examples of the stringent condition include the conditions described in reference literature [Molecular cloning—a Laboratory manual, 2nd edition (Sambrook, et al. 1989)], more specifically, a condition comprising incubation together with a probe in a solution containing 6×SSC (composition of 1×SSC: 0.15 M sodium chloride and 0.015 M sodium citrate, pH 7.0), 0.5% SDS, 5× Denhardt's solution, and 100 mg/mL herring sperm DNA, at 65° C. for 8 to 16 hours for hybridization; and a condition comprising hybridization under the above-described condition and then washing at 65° C. in a solution containing an about 0.1 M or lower salt, preferably in another arbitrary solution of 0.2× SSC or having an ionic strength of substantially the same degree. This polynucleotide preferably has a sequence identity of 85% or more to the nucleotide sequence of the polynucleotide according to (1), more preferably a sequence identity of 90% or more, and most preferably a sequence identity of 95% or more, 96% or more, 97% or more, 98% or more, or 99% or more.

The polynucleotide according to the present invention can be present in the form of RNA (e.g., mRNA) or in the form of DNA (e.g., cDNA or genomic DNA). The DNA may be a double strand or a single strand. The nucleotide sequence of SEQ ID NO: 2, which is an example of the polynucleotide according to the present invention, is cDNA encoding the polypeptide SEQ ID NO: 1. The polynucleotide according to the present invention may contain an additional sequence, such as an untranslated region (UTR) sequence.

The polynucleotide according the present invention may be obtained (isolated) by any-method without specific limitations and can be, for example, isolated by preparing a probe that can specifically hybridize with a part of the nucleotide sequence of the polynucleotide and screening a genomic DNA library or cDNA library with the probe. Alternatively, the polynucleotide may be synthesized in accordance with a nucleic acid-synthesizing method such as a phosphoramidite method.

Alternatively, the polynucleotide according to the present invention may be prepared using an amplification method, such as PCR. A large amount of a DNA fragment containing the polynucleotide according to the present invention can be produced by, for example, preparing primers from the sequences at the 5'-site and the 3'-site (or their complementary sequences) of cDNA of the polynucleotide; and amplifying the DNA region between both the primers by performing, for example, PCR using the primers and using genomic DNA (or cDNA) as a template.

Examples of the polynucleotide according to the present invention include cDNA (SEQ ID NOs: 2 and 4) derived from Japanese eel and variants (SEQ ID NO: 6) of the cDNA.

[3. Recombinant Vector]

The polynucleotide (e.g., DNA) according to the present invention can be inserted into an appropriate vector to be used as a recombinant vector. The vector may be, for example, an autonomously replicating vector (e.g., plasmid) or a vector that is incorporated into the genome of a host cell when introduced into the host cell and is replicated together with the incorporated chromosome.

The vector is preferably an expression vector. In the expression vector, the polynucleotide according to the present invention is functionally linked to elements (e.g., promoter) necessary for transcription. The promoter is a DNA sequence exhibiting a transcription activity in a host cell and can be appropriate selected depending on the type ox the host.

Examples of the promoters operable in bacterial cells include the promoters of *Bacillus stearothermophilus* maltogenic amylase gene, *Bacillus licheniformis* alpha-amylase gene, *Bacillus amyloliguefaciens* BAN amylase gene, *Bacillus Subtilis* alkaline protease gene, and *Bacillus pumilus* xylosidase gene; the phage Lambda $P_R$ or $P_L$ promoters; and *Escherichia coli* lac, tip, or tac promoters.

Examples of the promoters operable in insect cells include polyhedrin promoter, P10 promoter, *Autographa californica* polyhedrosis basic protein promoter, baculovirus immediate-early gene 1 promoter, and baculovirus 39K delayed-early gene promoter. Examples of the promoters operable in yeast cells include promoters derived from yeast glycolytic genes, alcohol dehydrogenase gene promoter, TP11 promoter, and ADH2-4c promoter. Examples of promoters operable in filamentous cells include ADH3 promoter and tpiA promoter.

Examples of the promoters operable in mammalian cells include SV40 promoter, MT-1 (metallothionein gene) promoter, and adenovirus-2 major late promoter.

In addition, the polynucleotide according to the present invention may be functionally bound to an appropriate terminator, such as human growth hormone terminator or TPI1 or ADH3 terminator for fungal host cells, as necessary. The recombinant vector according to the present invention may further include elements such as a polyadenylation signal, a transcription enhancer sequence, and a translation enhancer sequence.

The recombinant vector according to the present invention may further include a DNA sequence allowing the replication of the vector in host cells. An example thereof is SV40 replication origin (when the host cell is a mammalian cell).

The recombinant vector according to the present invention may further contain a selection marker. Examples of the selection marker include resistance genes to drugs such as ampicillin, kanamycin, tetracycline, chloramphenicol, neomycin, or hygromycin.

[4. Transformant]

The polynucleotide according to the present invention or the recombinant vector according to the present invention (generally referred to as nucleic acid construct of the present invention) are introduced into appropriate host cells to produce a transformant.

Examples of the host cells include bacterial cells, yeast cells, fugal cells, and higher eukaryotic cells. When culturing is performed under culturing conditions such that bilirubin is contained inside the host cells, the polypeptide of the present invention is produced in a state of being bound to bilirubin, whereas under culturing conditions such that bilirubin is not contained inside the host cells (for example, culturing conditions using a medium not containing lipoprotein), the polypeptide can be produced in a state of not being bound to bilirubin.

Examples of the bacterial cells include Gram-positive bacteria, such as *Bacillus* and *Streptomyces,* and Gram-negative bacteria, such as *Escherichia coli.* These bacterial cells may be transformed by, for example, a protoplast method or a method using competent cells.

Examples of the yeast cells include cells belonging to *Saccharomyces* or *Schizosaccharomyces,* such as *Saccharomyces cerevisiae* and *Saccharomyces kluyveri.* Examples of a method of introducing the nucleic acid construct of the present invention into yeast host cells include an electroporation method, a spheroplast method, and a lithium acetate method.

Examples of fungal cells other than yeast cells include cells belonging to Filamentous fungi, such as *Aspergillus, Neurospora, Fusarium,* and *Trichoderma.* Where Filamentous fungi are used as host cells, transformation can be carried out by incorporating nucleic acid constructs of the present invention into host chromosomes to prepare recombinant host cells. Incorporation of the nucleic acid constructs into host chromosome is carried out by, for example, homologous recombination or heterologous recombination.

When host cells are insect cells, both a recombinant gene-transfected vector and baculovirus are cotransfected into insect cells to prepare a recombinant virus in the insect cell culture supernatant, and insect cells are then infected with the recombinant virus to express proteins. Examples of the cotransfection include a calcium phosphate method and a lipofection method.

Examples of the mammalian cells include HEK 293 cells, HeLa cells, COS cells, BHK cells, CHL cells, and CHO cells. The mammalian cells can be transformed by, for example, an electroporation method, a calcium phosphate method, or a lipofection method.

The transformant is cultured in an appropriate culture medium under conditions allowing the expression of the introduced nucleic acid construct. Subsequently, the fluorescent polypeptide according to the present invention is optionally isolated and purified from the culture of the transformant.

The transformant is not limited to cells. That is, the transformant may be tissue, an organ, or an individual transformed with the nucleic acid construct according to the present invention. In some cases, however, the transformant other than cells is preferably non-human-derived one, and, in particular, the individual is preferably non-human-derived one.

[5. Complex of Fluorescent Polypeptide and Bilirubin, Etc.]

The present invention also encompasses a complex of the fluorescent polypeptide according to the present invention and bilirubin (holo form). This complex emits fluorescence by being irradiated with an excitation light having a prescribed wavelength. The fluorescent polypeptide according to the present invention can function as a carrier stably holding bilirubin. This complex may be a reconstructed complex prepared by isolating and purifying the fluorescent polypeptide (apo form) not binding to bilirubin and bringing the fluorescent polypeptide into contact with bilirubin.

A fusion polypeptide composed of a fluorescent polypeptide according to the present invention and another polypeptide (hereinafter, referred to as fusion polypeptide according to the present invention) is also encompassed in the present invention. Examples of the fusion polypeptide include fused protein produced by expression of the recombinant vector according to the present invention; fused protein prepared by labelling arbitrary protein by the fluorescent polypeptide according to the present invention; fused protein prepared by fusion of the fluorescent polypeptide according to the present invention and a prescribed peptide sequence for stabilizing fluorescence; and a probe for FRET including the fluorescent polypeptide according to the present invention and another fluorescent polypeptide. That is, the type of the polypeptide that is fused with the fluorescent polypeptide according to the present invention is not particularly limited.

Antibodies that specifically bind to the fluorescent polypeptide according to the present invention are also encompassed in the present invention.

[6. Detection of Bilirubin in Subject]

The bilirubin detecting method according to the present invention includes 1) a contact step for bringing a fluorescent polypeptide according to the present invention or a fusion polypeptide according to the present invention into contact with a subject for detecting bilirubin and 2) a detection step for detecting the fluorescence emitted from the polypeptide or the fusion polypeptide, after the contact step.

(Contact Step)

The subject for detecting bilirubin may be any subject that is intended to be used for detecting whether the subject contains bilirubin or not or for measuring the content of bilirubin. Examples of the subject include biological samples and non-biological samples. The biological samples are not particularly limited, and examples thereof include cells themselves, cell extracts, and samples derived from body fluids (e.g., samples derived from blood, saliva, lymph, cerebrospinal fluid, or urine). Among these samples, preferred are samples derived from body fluids; and more preferred are samples derived from blood or urine. Examples of the samples derived from blood include blood itself, serum, and plasma collected from a living body. The living body may be a human or a non-human vertebrate, but preferred are human and non-human mammals, and more preferred is human. Examples of the cell itself or the cell extract include spleen cells (in particular, reticular cells), hepatocytes, and extracts from these cells. Examples of the non-biological samples include bilirubin reference samples containing bilirubin at prescribed concentrations.

The method for bringing the fluorescent polypeptide or fusion polypeptide according to the present invention into contact with a subject may be appropriately selected depending on the type of the subject. For example, when the subject to be used in the detection has a gene translation system, such as cell itself, the contact step may be performed by introducing a polypeptide encoding the fluorescent polypeptide or fusion poly-peptide according to the present invention into the subject. When the subject to be used in the detection is other than cell itself, the contact step may be preformed by, for example, bringing the isolated fluorescent polypeptide or fusion polypeptide according to the present invention into direct contact with the subject (mixing the both).

The conditions for the contact step are those not substantially causing denaturation in the fluorescent polypeptide or fusion polypeptide according to the present invention. The conditions not substantially causing denaturation in these polypeptides are, for example, a temperature range of 4° C. or more and 65° C. or less, preferably a temperature range of 20° C. or more and 37° C. or less. The contact step may be performed in physiological saline or in a buffer solution, such as a phosphate buffer, as necessary.

(Detection Step)

The detection step is performed after the contact step and detects the fluorescence emitted by the polypeptide or fusion polypeptide according to the present invention. The fluorescence may be detected by any method. For example, the presence or absence of fluorescence emission or the fluorescence intensity may be measured using a fluorescence-detecting system, such as a UV transilluminator or LED transilluminator, a fluorescence microscope, a fluorescence detector, or a flow cytometry. The measurement of the presence or absence of fluorescence emission can detect whether bilirubin is contained (presence of fluorescence emission) or not (absence of fluorescence emission) in the subject. The measurement of the fluorescence intensity can detect the content of bilirubin in the subject.

The content of bilirubin in a subject may be a relative content of bilirubin compared to a reference sample or an absolute content of bilirubin (absolute concentration). In order to determine the absolute content of bilirubin, for example, a calibration curve may be prepared in advance using bilirubin standard samples having known concentrations.

(Testing Step)

The bilirubin detecting method according to the present invention may further include a testing step for inspecting the presence or absence of a predisposing factor or onset of liver disease based on the detection results in the detection step, as necessary.

Bilirubin in vertebrates is one of degradation products of heme. In degradation of erythrocytes in spleen, heme is degraded in reticular cells of the spleen into bilirubin (unconjugated). The resulting bilirubin is transported to the liver in a form of binding to albumin.

In blood tests, the amount of unconjugated bilirubin is evaluated as an item of indirect bilirubin level, which is determined by measuring the amount of total bilirubin and the amount of direct bilirubin (conjugated bilirubin) and subtracting the amount of direct bilirubin from the amount of total bilirubin.

In blood tests, the amount of indirect bilirubin is established as one index showing a liver function. Accordingly, it is possible to inspect the presence or absence of a predisposing factor or onset of, for example, liver disease or hemolytic disease by determining the content of bilirubin in a subject (in particular, a sample derived from blood) by the bilirubin detecting method according to the present invention.

Examples of the liver disease as the inspection object include various hepatic dysfunctions. More specifically, examples of the liver disease or hemolytic disease include hepatitis, cirrhosis, liver cancer, hepatobiliary disease, hemolytic anemia, and constitutional jaundice (Gilbert's syndrome and Crigler-Najjar syndrome). In particular, examples of the disease the index of which is unconjugated bilirubin level include hemolytic jaundice, fulminant hepatitis, constitutional jaundice, and nuclear jaundice observed in newborn.

The reference in inspection for the presence or absence of a predisposing factor or onset of liver disease may be, for example, the reference in a conventional blood test (a normal range of indirect bilirubin level: 0.8 mg/dl or less), when the subject is a sample derived from blood.

The bilirubin detecting method according to the present invention directly measures the amount of unconjugated bilirubin. The amount of total bilirubin can also be determined by combining the result of this direct measurement and the result of direct measurement of the amount of conjugated bilirubin (measurable by, for example, a vanadic acid oxidation method or diazo coupling method).

Throughout the specification, the term "diagnosing" or "diagnosis" refers to identification of a disease or pathological condition by a doctor based on the symptom or sign in a patient. Throughout the specification, the term "testing" or "test" refers to a test for the presence or absence of a predisposing factor or onset of, for example, liver disease or hemolytic disease in human or non-human animal (also referred to as "subject") as an object to be tested, not accompanied by identification (diagnosis) by a doctor. The test result obtained by the detecting method according to the present invention can be one material for diagnosis by a doctor.

(Other Application Example of Bilirubin Detecting Method)

Another application example of the bilirubin detecting method according to the present invention is a method for detecting a biological material that is contained in a subject derived from an organism, such as a biological sample, and has capacity of binding to bilirubin. The biological material is indirectly detected by bilirubin detection in the subject. For example, the amount of HDL cholesterol in a subject (in particular, a sample derived from blood) is measured. HDL cholesterol specifically binds to bilirubin.

[7. Bilirubin Detecting Kit]

A bilirubin detecting kit according to the present invention includes at least one selected from 1) a fluorescent polypeptide according to the present invention, 2) a polynucleotide encoding the fluorescent polypeptide according to the present invention, 3) a recombinant vector according to the present invention, 4) a transformant according to the present invention, and 5) a fusion polypeptide according to the present invention. This detection kit preferably includes at least one selected from components 1) to 3) and 5).

The detection kit according to the present invention optionally includes at least one of reagents and tools (such as buffer solutions and pipettes) for detecting bilirubin; reagents and tools (such as test tubes and buffer solutions) for preparing samples (subjects for detection); a manual of the detection kit; a sample for a control in detection; reference data for analyzing detection results; and other affixations. The manual of the detection kit explains the content of the detecting method according to the present invention, described in the above paragraph [6. Detection of bilirubin in subject].

[8. Polypeptide Immobilized to Substrate]

In an embodiment of the polypeptide according to the present invention, the polypeptide is immobilized to a substrate. The polypeptide may be applied and immobilized to a substrate of any material. Specifically, examples of the material include polystyrene; magnetic beads; sterilized paper; sterilized filter paper; sterilized nonwoven fabric; hydrophilic membranes, such as polyvinylidene fluoride (PVDF) membranes and polytetrafluoroethylene (PTFE)

membranes; polymer materials having flexibility, such as silicone rubber; biodegradable polymers, such as polyglycolic acid and polylactic acid; agar media; hydrogels, such as collagen gels and gelatin gels; and gold thin films. Such a polypeptide immobilized to a substrate is appropriately used in, for example, the detection of bilirubin.

The substrate may have any shape. Specifically, examples of the shape include plate shapes (i.e., basal plate or sheet) and spherical shapes. Specifically, examples of a product including the substrate onto which the polypeptide immobilized include sheets, microchips, beads, and sensor chips. Examples of the sheets include fibrous, nonwoven, and film-like membranes.

The method of applying and immobilizing the polypeptide according to the present invention to a substrate may be appropriately selected depending on the material of the substrate. Specifically, for example, an avidin-biotin method, an antigen-antibody method, or an affinity tag method using a His-tag can be used. From the viewpoint of convenience, the affinity tag method is preferred. Examples of the method of immobilizing the polypeptide of the present invention to a sheet-like substrate include a method of applying the polypeptide of the present invention to the sheet-like substrate (e.g., application by dipping, air spray, or ink-jetting); a method of dropping, transcribing, or seeding of the polypeptide of the present invention onto the substrate; and a method of dropping, transcribing, or seeding of the polypeptide of the present invention and then performing air-drying or lyophilization.

[9. Specific Embodiments According to the Present Invention]

That is, the present invention encompasses any of the following aspects 1) to 11):

1) A polypeptide shown in any of the following (1) to (4) and having fluorescent properties in the presence of bilirubin:
(1) a polypeptide including the amino acid sequence of SEQ ID NO: 1, (2) a polypeptide including an amino acid sequence having substitution, deletion, insertion, and/or addition of 1 to 21 amino acids in the amino acid sequence of SEQ ID NO: 1, (3) a polypeptide having 85% or more sequence identity to the amino acid sequence of SEQ ID NO: 1, and (4) a polypeptide including the amino acid sequence encoded by a polynucleotide that hybridizes with a polynucleotide consisting of a sequence complementary to a polynucleotide encoding the polypeptide according to the above (1) under a stringent condition;

2) The polynucleotide according to any of the following (1) to (4): (1) a polynucleotide encoding a polypeptide including the amino acid sequence of SEQ ID NO: 1, (2) a polynucleotide encoding a polypeptide including an amino acid sequence having substitution, deletion, insertion, and/or addition of 1 to 21 amino acids in the amino acid sequence of SEQ ID NO: 1 and having fluorescent properties in the presence of bilirubin, (3) a polynucleotide encoding a polypeptide having 85% or more sequence identity to the amino acid sequence of SEQ ID NO: 1 and having fluorescent properties in the presence of bilirubin, and (4) a polynucleotide hybridizing with a polynucleotide consisting of a sequence complementary to the polynucleotide according to the above (1) under a stringent condition and encoding a polypeptide having fluorescent properties in the presence of bilirubin;

3) The polypeptide according to aspect 1), wherein the polypeptide has a dissociation constant for bilirubin of 0.1 nM or more and 100 nM or less;

4) A recombinant vector comprising the polynucleotide according to aspect 3);

5) A transformant comprising the polynucleotide according to aspect 3) or the recombinant vector according to aspect 4);

6) A fusion polypeptide comprising the polypeptide according to aspect 1) or 3) and another polypeptide;

7) A polypeptide-bilirubin complex constituted by bringing bilirubin into contact with the polypeptide according to aspect 1), 3) or 6) in a form free from bilirubin;

8) A method for detecting bilirubin in a subject, the method comprising:
a contact step of bringing the polypeptide according to aspect 1), the polypeptide according to aspect 3), or the fusion polypeptide according to aspect 5) into contact with the subject; and
a detection step of detecting fluorescence emitted by the polypeptide or the fusion polypeptide, after the contact step;

9) The method according to aspect 7), wherein the subject is a sample derived from blood or urine collected from a living body;

10) The method according to aspect 8) or 9), further comprising:
a testing step of inspecting the presence or absence of a predisposing factor or onset of liver disease or hemolytic disease based on the detection results in the detection step; and 11) A bilirubin detecting kit comprising at least one selected from the polypeptide according to aspect 1), the polynucleotide according to aspect 2), the polypeptide according to aspect 3), the recombinant vector according to aspect 4), the transformant according to aspect 5), and the fusion polypeptide according to aspect 6).

This application is based on Japanese Patent Application No. 2013-040097 (Filing date: Feb. 28, 2013), which is hereby incorporated by reference herein in its entirety.

EXAMPLES

Example 1

[1. Cloning of UnaG Gene Derived from Japanese Eel]
(Material and Method)
<Experimental Material>

Glass eel (obtained from Kenis Limited), fry of natural Japanese eel (*Anguilla japonica*), was used.

<Preparation of Total RNA from Glass Eel>

Living glass eel (about 0.2 g) was immediately frozen in liquid nitrogen and was then pulverized in liquid nitrogen with a teflon homogenizer. To the glass eel in the homogenizer vessel was added 3 mL of TRIzol (registered trademark) reagent. The glass eel was dissolved on ice and was homogenized in a low-temperature room. The homogenate was transferred into a conical tube, and 0.6 mL of chloroform was added thereto. The homogenate containing the chloroform was stirred and left to stand at room temperature for 5 min. After centrifugation at 7,000 rpm at 4° C. for 20 min, the aqueous layer was collected (about 1.5 mL). To the collected aqueous layer was added 1.5 mL of isopropanol. The mixture was stirred and was left to stand at room temperature for 10 min, followed by centrifugation at a rotation speed of 15,000 rpm at 4° C. for 10 min. The supernatant was removed. The precipitate was rinsed with 75% ethanol and was then centrifuged at a rotation speed of 10,000 rpm at 4° C. for 5 min to remove the ethanol and to obtain a precipitate. The resulting precipitate was air-dried and was dissolved in 100 µL of RNase-free water to obtain total RNA of Japanese eel. The resulting total RNA was measured for the absorbance at a wavelength of 260 nm (hereinafter notated as $A_{260}$, and absorbance at a different wavelength is also similarly notated) to determine the concentration of RNA (converted at 1 $A_{260}$ a 40 ng RNA/μL).

<Obtaining of UnaG Gene Full Length Through Cloning by 5'-RACE Method and 3'-RACE Method>

Based on information on nine amino acid fragment sequences of the fluorescent protein of eel isolated and identified by Hayashi, et al. (Hayashi, et al., Fish. Sci., 75, 1461-1469, 2009), the degenerate primers of SEQ ID NOs: 7 to 16 were designed. In addition, the adaptor primers of SEQ ID NOs: 17 to 23 for RACE were designed, and the gene encoding the fluorescent protein of Japanese eel was cloned by 3'-RACE method and 5'-RACE method. The procedure of the cloning will be described in detail below. The nucleotide sequences of the primers of SEQ ID NOs: 7 to 23 used for the cloning are also shown in Table 1.

TABLE 1

| Primer name | Sequence (5'→3') | Position in cDNA |
|---|---|---|
| peptide3 | GCNATHGGNGCNCCNAAR | nt67-84 |
| peptide5 | YTNGTNTAYGTNCARAAR | nt298-306 |
| peptide6 | TGGGAYGGNAARGAR | nt307-321 |
| peptide6 nested | AARGARACNACNTAY | nt316-330 |
| peptide7 | GARYTNWSNGAYGGNGGNGAY | nt85-105 |
| peptide7 nested | GAYGGNGGNGAYGCNGCN | nt94-111 |
| peptide8 | ATHGCNGAYWSNCAYAAYTTY | nt31-51 |
| peptide8 nested | CAYAAYTTYGGNGARTAY | nt43-60 |
| peptide9 | GARYAAYGGNCCNCCNACNTTY | nt166-186 |
| peptide9 nested | ACNTTYYTNGAYACNGAR | nt181-198 |
| 5' RACE abridged anchor primer | GGCCACGCGTCGACTAGTACGGGIIGGGIIGGGIIG | 5'-end |
| 5' RACE peptide6 GSP1 | GCQCTCCGGTAGCTGCGCACAGCC | nt387-410 |
| 5' RACE peptide6 GSP2 | GCGCACAGGCACGACGTGTOCC | nt375-396 |
| 5' RACE peptide9 GSP1 | GTAGGTACAGCAGCTTCTCTCCCACC | nt276-301 |
| 5' RACE peptide9 GSP2 | CTCTCCCACCAAGTTCACCACA | nt264-285 |

TABLE 1-continued

| Primer name | Sequence (5'→3') | Position in cDNA |
|---|---|---|
| 5' up-stream | GCTTTGCGAGCATCTACTTTTTATTGTCC | 5'-upstream region |
| 3' RACE SpeI-NotI-d(T)15 | GACTAGTTCTAGATCGCGAGCGGCCGCCCT15 | 3'-end poly-A tail |

To 5 μg of the total RNA were added 0.5 μL of 100 μM SpeI-NotI-d(T)15 primer (SEQ ID NO: 23) and 1 μL of 10 nM dNTP mixture. The volume of the mixture was adjusted to 13 μL with water. After heating at 65° C. for 15 min, the mixture was promptly cooled with ice. To the mixture were added 4 μL of 5× First-Strand Buffer (250 mM Tris-HCl (pH 8.3), 375 mM KCl, and 15 mM $MgCl_2$), 1 μL of 0.1 M DTT, 40 units of recombinant RNase inhibitor RNase OUT (trademark) (Invitrogen), and 200 units of SuperScript III (trademark) reverse transcriptase (Invitrogen), followed by heating at 50° C. for 60 min and then at 70° C. for 15 min. Subsequently, 1 μL of ribonuclease H was added thereto, followed by incubation at 37° C. for 20 min to prepare 1st strand cDNA for 3'-RACE. Separately, 1st strand cDNA for 5'-RACE was prepared using 5'-RACE System for Rapid Amplification of cDNA Ends, Version 2.0 (Invitrogen) in accordance with the procedure manual attached to the product. PCR was performed using the degenerate primers designed as described above and the adaptor primers for 3'-RACE and 5'-RACE. The amplified product was cloned into pT7Blue T-Vector (Novagen) and was subjected to DNA sequence analysis with Applied Biosystems 3730xl DNA Analyzer (Applied Biosystems). The sequence was determined using gene analysis software, DNAdynamo (Blue Tractor Software Ltd.).

(Result)

The 5'-end, the 3'-end, and other regions of full-length cDNA obtained by the above-described method were united based on the overlapping of the sequences to obtain the 420 bp nucleotide sequence of SEQ ID NO: 2. This sequence was used as the flail-length cDNA sequence of the UnaG gene. In addition to the nucleotide sequence of SEQ ID NO: 2, the nucleotide sequence of SEQ ID NO: 4 was also obtained as a variant of SEQ ID NO: 2. The following experiments were all performed based on the sequence of SEQ ID NO: 2.

Furthermore, a deduced amino acid sequence including 139 amino acids of SEQ NO: 1 was prepared based on the cDNA sequence of SEQ ID NO: 2. The polypeptide indicated by this amino acid sequence is referred to as UnaG protein. UnaG protein did not have an amino acid sequence, X-Y-G (X represents an arbitrary amino acid), that is included in the amino acid sequences of GFP and GFP-like protein and forms a chromophore.

[2. Expression of Recombinant UnaG Protein]

[2-1. Expression of UnaG Protein (Apo Form) in *Escherichia Coli*]

(Material and Method)

<Production of Recombinant (Vector) for *Escherichia Coli* Expression>

A DNA fragment including the sequence of full-length UnaG gene prepared above was ligated to the restriction enzyme sites, BamHI and EcoRI, of *Escherichia coli* expression vector pGEX-217 (GE Healthcare) including a GST-tag sequence that can express the GST-fused protein in *Escherichia coli* and transformed into *Escherichia coli* strain DH5α for subcloning. Thus, a UnaG (apo form) expression vector (pGEX-2T-UnaG) for *Escherichia coli* was constructed.

<Expression of Recombinant (Vector) for *Escherichia Coli* Expression in *Escherichia Coli*, Culturing Thereof, and Purification of Protein>

The constructed expression vector (pGEX-2T-UnaG) was transformed into *Escherichia coli* strain BL21 (DE3). The transformant was cultured on a plate of an LB solid medium to obtain colonies. The resulting colonies were inoculated in 40 mL of an LB liquid medium and were cultured overnight at 37° C. Here, a glycerol stock of the resulting *Escherichia coli* solution was produced, and this glycerol stock was used as the recombinant (vector) for *Escherichia coli* expression in the experiments described below. The LB medium was scaled up to 400 mL using the culture solution, followed by culturing at 37° C. for 1 hr ($A_{600}$≈1.0). Subsequently, isopropyl-1-thio-β-D-galactoside (IPTG) was added to the LB medium to give a final concentration of 0.4 mM, followed by shaking at 17° C. for 6 hr to induce expression of UnaG protein. *Escherichia coli* cells were collected by centrifugation at a rotation speed of 8,000 rpm for 3 min.

The bacterial cells collected in the above-described process were suspended in 20 mL of phosphate buffered saline (PBS), and 200 μL of lysozyme (4 mg/mL) was added thereto. The bacterial cells were frozen with liquid nitrogen and were then thawed. This freeze and thaw process was repeated three times. After ultrasonication for 3 min, the supernatant of centrifugation at a rotation speed of 7,000 rpm at 4° C. for 20 min was collected to obtain a lysate of the bacterial cells. The lysate and 1 mL of Glutathione Sepharose 4B (GE Healthcare, carrier for GST) equilibrated with PBS were incubated at 4° C. for 1 hr to immobilize the GST-fused UnaG protein to the carrier. The carrier was rinsed with PBS in a volume of 10 times or more the total volume of the carrier, and 80 units of thrombin (GE Healthcare) were then added to the carrier, followed by digestion reaction at room temperature overnight to cleave UnaG protein from the GST immobilized to the carrier. In addition, 1 mL of Benzamidine Sepharose 6B (GE Healthcare, carrier for thrombin) equilibrated with PBS was added to UnaG protein solution, followed by incubation at 4° C. for 1 hr. Thus, thrombin was allowed to bind to the carrier and was thereby collected. The carrier was removed to obtain the supernatant as purified UnaG protein. The purified UnaG protein was obtained in an amount of 2.0 to 2.5 mg. The purified UnaG protein was subjected to SDS PAGE electrophoresis for verification of the degree of purification. The results are shown in FIG. 1 and are collectively described in paragraph 2-2. below.

<Measurement of Protein Concentration>

Protein concentration was calculated as follows. In measurement of protein concentration in the experimental methods described in paragraphs [2. Expression of recombinant UnaG protein] to [7. Detection of bilirubin in human serum], the calculations were all performed by the same method.

The molar extinction coefficient ($\varepsilon_M$) of UnaG protein at 280 nm was first calculated (C. N. Pace, et al. Protein Sci. 4, 2411-2423, 1995). Then, based on the resulting $\varepsilon_M$ value and absorbance $A_{280}$, the protein concentration was determined by the following computation expressions:

$\varepsilon_M = Trp(2) \times 5500 + Tyr(5) \times 1490 + Cystine(0) \times 125 = 18450 (A_{280}/\text{mol/cm})$; and Protein concentration=$A_{280}/\varepsilon_M = A_{280}/18450 (\text{mol}/\text{dm}^3)$.

[2-2. Expression of UnaG Protein (Holo Form) in Mammalian Cell]

(Material and Method)

<Production of Recombinant (Vector) for Mammalian Cell Expression>

DNA to be inserted to an expression vector for mammalian cell was amplified by PCR using full-length cDNA of the UnaG gene of SEQ ID NO: 2 as template DNA, a sense primer (SEQ ID NO: 24), and an antisense primer (SEQ ID NO: 25). A FLAG-tag sequence (SEQ ID NO: 26) was inserted into the KpnI restriction enzyme site and the BamHI restriction enzyme site of expression vector pcDNA3 (Invitrogen) for mammalian cell, and the amplified DNA fragment was ligated to the BamHI restriction enzyme site and the EcoRI restriction enzyme site of the resulting pcDNA3-FLAG vector and transformed into *Escherichia coli* strain DH5α for cloning. The vector was extracted from *Escherichia coli* and was purified. The sequence was confirmed by DNA sequence analysis. Thus, a UnaG expression vector (pcDNA3-FLAG-UnaG) for mammalian cells was constructed.

<Expression of Recombinant (Vector) for Mammalian Cell Expression in Mammalian Cell, Culturing Thereof, and Purification of Protein>

HEK293T cells were seeded in 20 dishes of 10 cm in diameter and were cultured in a Dulbecco's Modified Eagle Medium (high glucose, GIBCO) containing 10% fetal bovine serum (manufactured by GIBCO) and antibiotics (penicillin and streptomycin) under conditions of 5% $CO_2$ and a temperature of 37° C. After proliferation of the cells until 50% to 60% confluent, the medium in each dish was changed to a medium not containing antibiotics, Plasmid DNA of the mammalian cell UnaG expression vector and a transfection reagent (10 μg of DNA, 40 μL of FuGene (registered trademark) HD transfection reagent, and 500 μL of Opti-MEM (registered trademark) I Reduced-Serum Medium (GIBCO), for each dish of 10 cm in diameter) were mixed in advance, and 500 μL of the mixture was added to each dish for transfection. After the transfection, the cells were cultured overnight. The medium in each dish was changed to a medium containing the antibiotics. The cells were further cultured overnight to express protein.

After the expression of protein, the medium was removed from each dish, and the cells were rinsed with PBS. Subsequently, the cells were peeled from the dish by adding PBS to the dish and were suspended in PBS. The suspension was centrifuged at 1,000 rpm for 3 minutes to Collect the cells as precipitate. The cells were suspended in 20 mL of dissolution buffer [50 mM Tris-HCl (pH 7.4), 150 mM NaCl, 1 mM EDTA, and 1% Triton X-100] and were dissolved in the dissolution buffer by stirring with a rotator at room temperature for 15 min. Centrifugation was performed with a centrifugal force of 15,000 g at 4° C. for 10 min, and the supernatant was collected. The collected supernatant was incubated with 4 mL of ANTI-FLAG M2-Agarose Affinity Gel (Sigma-Aldrich Co., Ltd.) equilibrated with TBS buffer [50 mM Tris-HCl (pH 7.4) and 150 mM NaCl] at 4° C. for 3 hr. After the incubation, the supernatant was removed by centrifugation. The gel was rinsed with TBS buffer in a volume of 10 times or more the total volume of the gel. The FLAG-UnaG protein (hole form) was then eluted from the gel using TBS buffer [containing 100 μg/mL of FLAG peptide (Sigma-Aldrich Co., Ltd.)] in a volume of 5 times the total volume of the gel. Amicon Ultra-15 (3000MWCO, Merck Millipore Corporation) was used as the elution column. The eluate was concentrated by ultrafiltration and was applied to PD-10 column (GE Healthcare), followed by buffer change and removal of excessive FLAG peptide for purification to give purified FLAG-UnaG protein. The purified FLAG-UnaG protein (holo form) was irradiated with a UV transilluminator for verifying whether fluorescence was present or not. SDS-PAGE electrophoresis was further performed to verify the degree of purification. The results are shown in FIG. 1.

quantum yield were measured. The excitation spectrum and the fluorescence spectrum were measured with a spectrophotofluorometer, RF-5300PC (Shimadzu Corporation), at an excitation wavelength of 475 nm and a fluorescence wavelength of 550 nm. The absorption spectrum was measured with a spectrophotometer, U-2900 (Hitachi High-Technologies Corporation). The quantum yield was measured with an absolute quantum yield measurement system, Quantaurus-QY (Hamamatsu Photonics K.K.) at excitation wavelengths of 470 nm and 480 nm. A known fluorescent protein, EGFP, was similarly measured, and the values were compared to those of UnaG protein. The results are shown in Table 2.

(Result)

TABLE 2

|  | Maximum excitation/ fluorescence wavelength (nm) | Molar extinction coefficient ($M^{-1}$ $cm^{-1}$) | Quantum yield (%) | Brightness* | Number of amino acids | Molecular weight |
| --- | --- | --- | --- | --- | --- | --- |
| UnaG | 498/527 | 77,300 (498 nm) | 51 | 39.4 | 139 | 16.5K |
| EGFP | 490/509 | 49,550 (490 nm) | 60 | 29.7 | 238 | 27K |

*Brightness = [(Molar extinction coefficient) × (Quantum yield)]/1,000

(Result)

FIG. 1 includes diagrams showing expression of recombinant UnaG protein in *Escherichia coli* and mammalian cells. The diagram (a) shows observation results of *Escherichia coli* cell (2) expressing recombinant UnaG protein by irradiation with blue light using a UV transilluminator, where the diagram at the upper left shows *Escherichia coli* cells (1) transfected with vector pRSET as a control, and the diagram at the upper right shows *Escherichia coli* cells (3) expressing EGFP. The diagram (b) shows electrophoretic gels of SDS-PAGE electrophoresis of cell extracts of *Escherichia coli* cells (1) to (3) shown in diagram (a) stained by CBB staining. The diagram (c) includes a differential interference image and a fluorescence image by observation of mammalian cell HEK293T expressing recombinant UnaG protein under a fluorescence microscope. As shown in diagrams (b) and (c) of FIG. 1, the expression level of UnaG protein was sufficiently high in both *Escherichia coli* and mammalian cells. In addition, impurities could be sufficiently removed by the above-described purification process. However, as obvious from the microscopic photograph shown in diagram (a) of FIG. 1, UnaG protein expressed in *Escherichia coli* did not emit fluorescence in the *Escherichia coli* cells. In contrast, as obvious from the microscopic photograph shown in diagram (c) of FIG. 1, UnaG protein expressed in the mammalian cells emitted fluorescence.

These results demonstrate that UnaG protein has a fluorescent property in the presence of a ligand that is not contained in *Escherichia coli*, but is contained in mammalian cells. The ligand was presumed to be present in vertebrates, at least in both fishes and mammals.

[3. Analysis of Fluorescent Properties of UnaG Protein]
(Material and Method)
<Measurement of Fluorescence Spectrum, Absorption Spectrum, and Quantum Yield of UnaG Protein>

Figure 2:
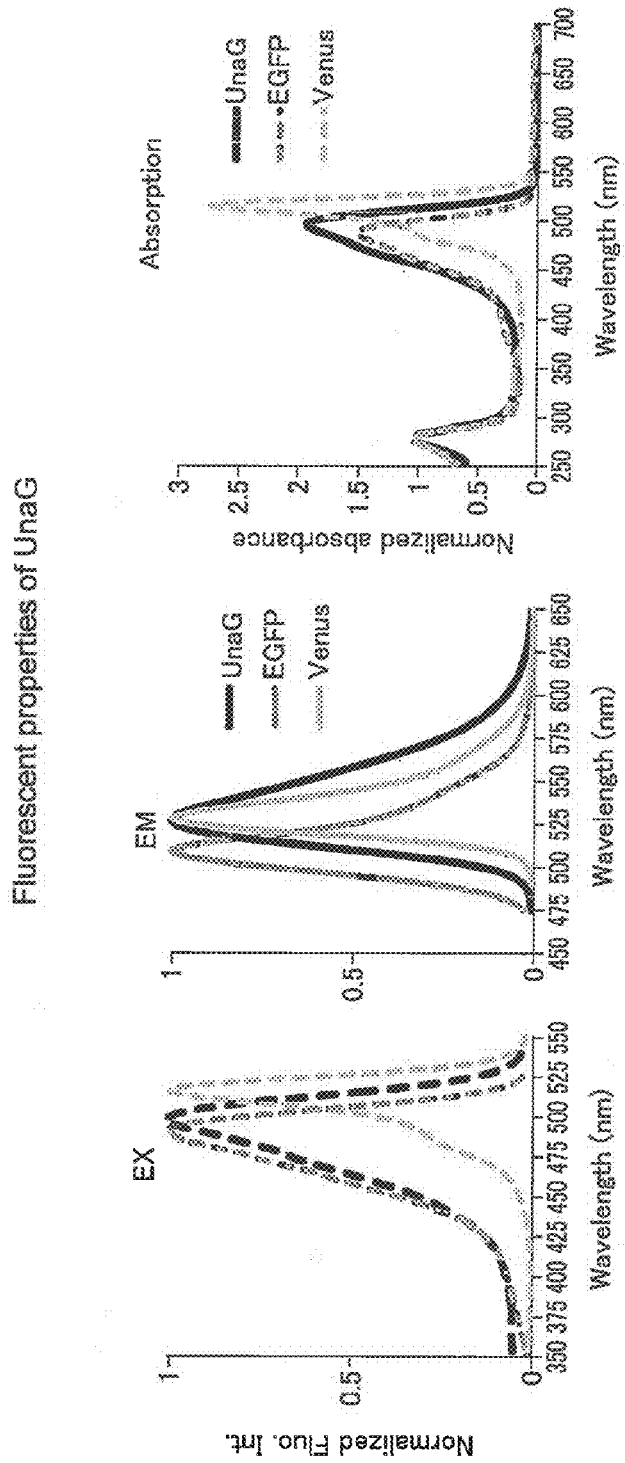
FIG. 2 includes graphs showing fluorescent properties of UnaG protein in Example of the present invention.

In order to analyze the fluorescent properties of UnaG protein, the fluorescence spectrum, absorption spectrum, and FIG. 2 includes graphs showing fluorescent properties of UnaG protein.

[4. Identification of Ligand UnaG Protein]
(Material and Method)
<Fractionation of Fetal Bovine Serum (FBS) by Density Gradient Centrifugation>

To 20 mL of FBS (GIBCO) was added 8 g (0.4 g KBr/mL) of KBr. The solution was diluted with PBS containing 0.4 g/mL KBr to give a total volume of 36 mL. This solution was dispensed into six centrifugal tubes, 6 mL each, and the dispensed solution was overlaid with 6 mL of 0.75% saline. Ultracentrifugation (Beckman Coulter, Inc.) was performed using the centrifugal tubes and Sw41Ti rotors (Beckman Coulter, Inc.) at 170,000 g at 15° C. for 20 hr. Subsequently, 0.33 mL of the fractional serum was pipetted from the upper layer in each centrifugal tube using a fraction collector (SK BIO International).

<Reconstruction of Apo UnaG Protein by FBS and FBS Fraction>

Apo UnaG protein produced by the method described in the above paragraph 2-1 above was used. Apo UnaG protein was added to a 10% FBS solution so as to give a concentration of 0.5 μM, followed by incubation at room temperature for 30 min for reconstruction.

UnaG protein reconstructed by FBS was measured for the excitation spectrum and the fluorescence spectrum.

Apo UnaG protein was added to an FBS fraction diluted two-fold with PBS so as to give a concentration of 0.5 followed by incubation at room temperature for 30 min. Subsequently, 200 μL of apo UnaG protein solution was added to each well of a 96-well microplate (Greiner Bio-One) and was subjected to measurement of the fluorescence intensity at a wavelength of 527 nm with excitation light having a wavelength of 497 nm using EnSpire multi-mode plate reader (PerkinElmer Co., Ltd.). The results are shown in FIG. 3.

(Result)

Figure 3:
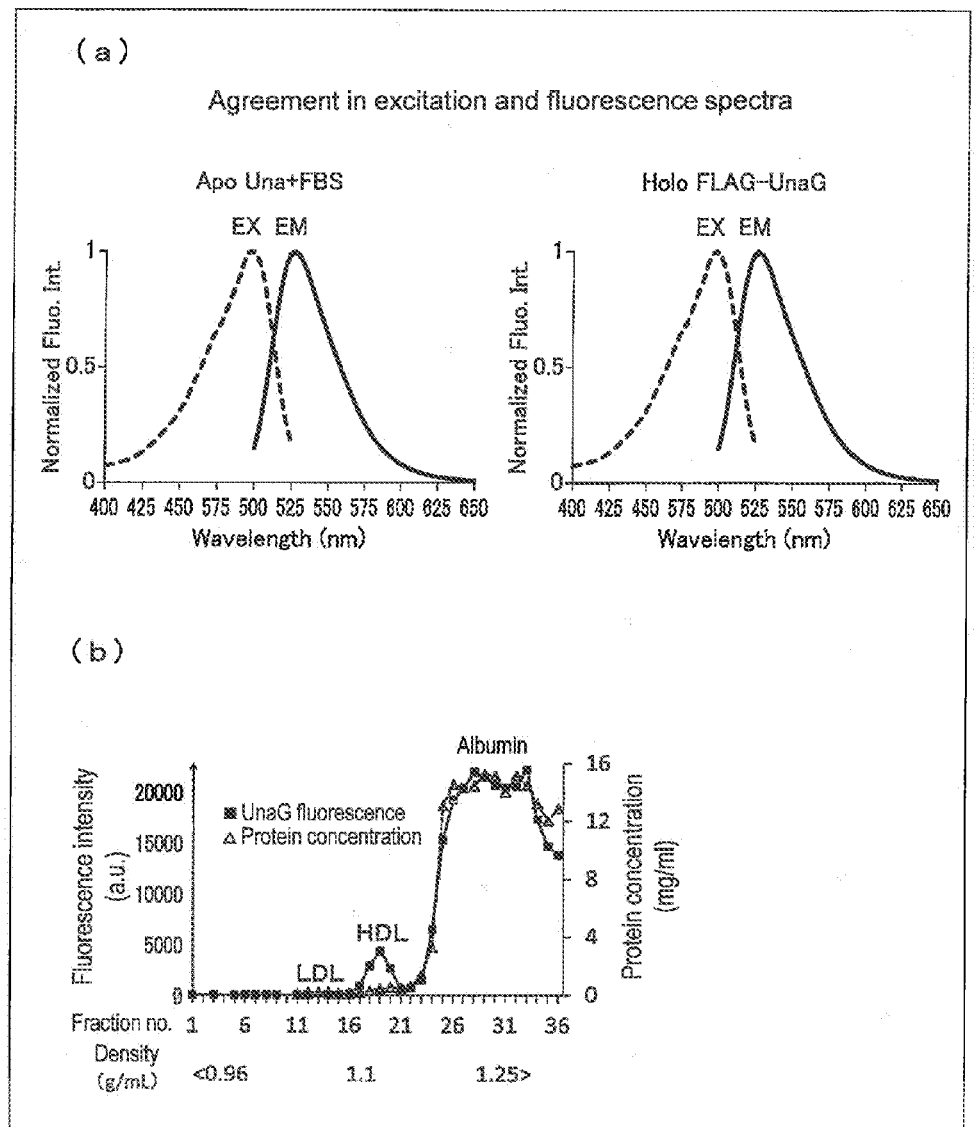
FIG. 3 includes graphs showing fluorescent properties of UnaG protein by reconstruction with fetal bovine serum (FBS) and an FBS fraction in Example of the present invention: the graphs (a) show excitation spectra and fluorescence spectra of apo UnaG protein reconstructed with HIS (left) and holo UnaG protein (FLAG-UnaG protein derived from mammalian cells) (right); and the graph (b) shows fluorescence intensity (solid line) measured by fractionating FBS by density gradient ultracentrifugation and reconstructing each fraction and apo UnaG protein, and protein concentration (broken line) of each serum fraction, where the vertical axis indicates fluorescence intensity (left axis) and protein concentration (mg/ml) (right axis), and the horizontal axis indicates fraction number.

FIG. 3 includes graphs showing, for example, fluorescent properties of UnaG protein by reconstruction with FBS and an PBS fraction. The graphs (a) show excitation spectra and fluorescence spectra of apo UnaG protein reconstructed with FBS (left) and holo UnaG protein (FLAG-UnaG protein derived from mammalian cells) (right). The graphs (b) show fluorescence intensity (solid line) measured by fractionating FBS by density gradient ultracentrifugation and reconstructing each fraction and apo UnaG protein, and protein concentration (Token line) of each serum fraction, where the vertical axis indicates fluorescence intensity (left axis) and protein concentration (mg/mL) (right axis), and the horizontal axis indicates fraction number.

The results shown in FIG. 3 demonstrate that a component contained in FBS functions as a ligand of UnaG protein.

<Extraction of Ligand from Holo UnaG Protein>

Extraction of ligands was performed in accordance with a Bligh and Dyer method (Bligh, E. G. & Dyer, W. J., Can. J. Biochem. Physiol., 37, 911-917, 1959). To 0.4 mL of solution of FLAG-UnaG protein (hole form) derived from mammalian cells, 0.5 mL of chloroform and 1 mL of methanol were added and mixed. To the mixture, 0.5 mL of chloroform and 0.5 mL of buffer were further added and mixed to give a mixture of an aqueous solution methanol:chloroform at a final ratio of 0.9:1:1. The mixture was then centrifuged at a centrifugal force of 1,500 rpm for 5 min to separate into an organic solvent layer containing the extracted lipid component including ligands and an aqueous layer. The lipid extract (i.e., the organic solvent layer) containing ligands was collected.

<Comparison of Absorption Spectra of Ligand Extracted from Holo UnaG Protein and Bilirubin>

Figure 4:
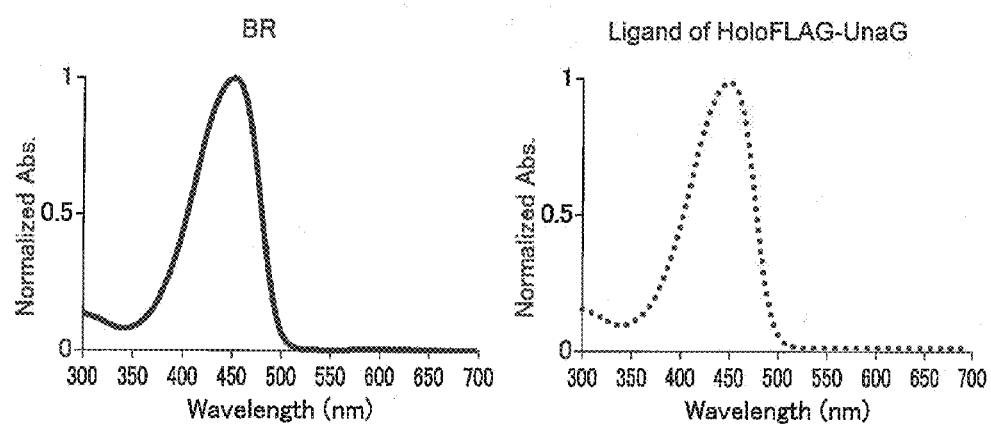
FIG. 4 includes graphs showing absorption spectra of bilirubin (left) and a ligand (right) extracted from holo UnaG in Example of the present invention, where the horizontal axis indicates the wavelength of absorbed light, and the vertical axis indicates absorbance.

The absorption spectra of the ligands extracted from bob UnaG protein by the above-described method were compared to that of one component, bilirubin, contained in serum for searching a ligand showing the same absorption spectrum The results are shown in FIG. 4.

(Result)

FIG. 4 includes graphs showing absorption spectra of bilirubin (left) and UnaG ligand (right), where the horizontal axis indicates the wavelength of the absorbed light, and the vertical axis indicates absorbance. As shown in FIG. 4, the absorption spectrum of UnaG ligand agreed with that of bilirubin, which demonstrates that the ligand of UnaG is bilirubin.

[5. Properties of UnaG Protein Against Unconjugated Bilirubin]

(Material and Method)

<Production of Holo UnaG by Reconstruction>

Bilirubin (Wako Pure Chemical Industries, Ltd.) dissolved in 100% DMSO was diluted with PBS and was added to an apo UnaG protein solution such that the molar ratio of bilirubin to apo UnaG was 2:1, followed by mixing. The mixing was controlled such that the final concentration of DMSO in the bilirubin solution and the final concentration of DMSO in the apo UnaG protein solution were the same. The container containing the solution mixture was shielded from light and was left to stand at room temperature for 10 min. The solution mixture was then supplied to a PD-10 column (GE Healthcare), and excessive bilirubin was removed, while the buffer contained in the solution mixture being changed to PBS. The holo UnaG protein was concentrated by ultrafiltration using Amicon Ultra (3000MWCO, Merck Millipore Corporation), as necessary.

<Reconstruction of Apo UnaG Protein Using Bilirubin or Bilirubin Analog>

Bilirubin or a bilirubin analog, biliverdin (Toronto Research Chemicals), urobilin (MP Biomedicals), or ditaurobilirubin (Frontier Scientific), was diluted with PBS such that the final concentration was 0.125 µM, 0.25 µM, 0.5 µM, 1.0 µM, or 2.0 µM and was mixed with 0.5 µM apo UnaG protein. The mixture was left to stand at room temperature for 30 min. Subsequently, 200 µL of the mixture was added to each well of a 96 well microplate (Greiner Bio-One) and was subjected to measurement of the fluorescence intensity at a wavelength of 527 nm with excitation light having a wavelength of 497 nm using EnSpire multi-mode plate reader (PerkinElmer Co., Ltd.). The results are shown in FIG. 5.

(Result)

Figure 5:
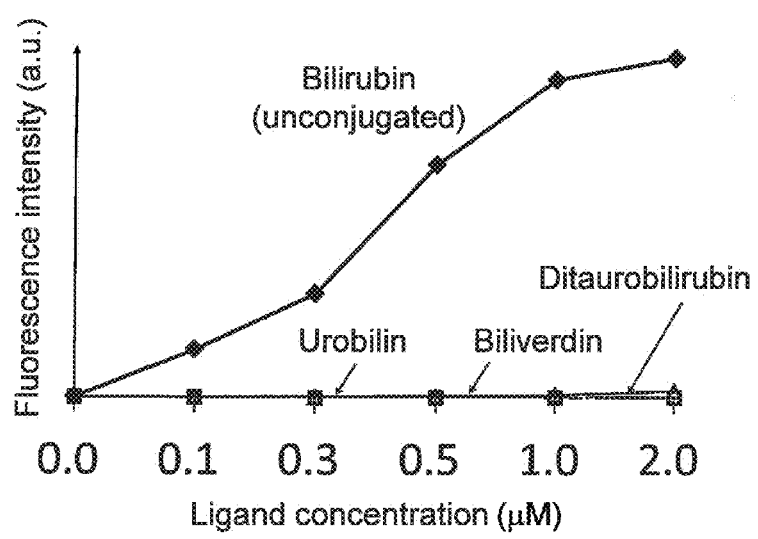
FIG. 5 is a graph showing specificity of UnaG protein in Example of the present invention to unconjugated bilirubin. Apo UnaG (0.5 µM) was mixed with a ligand: bilirubin (unconjugated) at various concentrations or a bilirubin analog, biliverdin, urobilin, or ditaurobilirubin, at various concentrations, and the fluorescence intensity at each concentration was measured. The vertical axis indicates fluorescence intensity, and the horizontal axis indicates concentration (µM) of each ligand.

FIG. 5 shows the fluorescence intensity of UnaG protein reconstructed by adding bilirubin or a bilirubin analog at each concentration to the apo UnaG protein solution. The horizontal axis indicates ligand concentration (µM), and the vertical axis indicates fluorescence intensity. UnaG did not emit fluorescence by addition of the bilirubin analogs, which demonstrates that the fluorescence of UnaG is specific to bilirubin.

[6. Analysis of Site Involving in Aggregability of UnaG Protein]

(Material and Method)

<Method for Producing Mutated UnaG by Mutation (R82EK84E) and Expression of R82EK84E Mutated UnaG Protein>

Site specific mutation was performed against the amino acid sequence of UnaG using GENEART (registered trademark) Site-Directed Mutagenesis System (Invitrogen) in accordance With the procedure manual attached to the product. The 82nd amino acid, R, and the 84th amino acid, K, of wild-type UnaG protein were substituted by E through PCR using the recombinant (vector) pGEX-2T-UnaG for *Escherichia coli* expression described in the above-mentioned paragraph 2-1. as a template and using a sense primer (SEQ ID NO: 27) and an antisense primer (SEQ ID NO: 28). The mutated pGEK-2T-UnaG (R82EK84E) was transformed into *Escherichia coli* strain BL21 (DE3), and protein was expressed by the same method as that described in paragraph 2-1. for expressing wild-type UnaG protein. UnaG protein was also purified by the same method as that described in paragraph 2-1. except that thrombin digestion was performed using 40 units of thrombin under conditions of a temperature of 20° C. for 3 hr. After purification, the holo form was prepared by reconstruction with bilirubin. The holo form was prepared by the same method as that described in paragraph 2-2. The deduced R82EK84E mutated amino acid sequence is shown in SEQ ID NO: 5.

<Evaluation of Aggregability of Protein>

Figure 6:
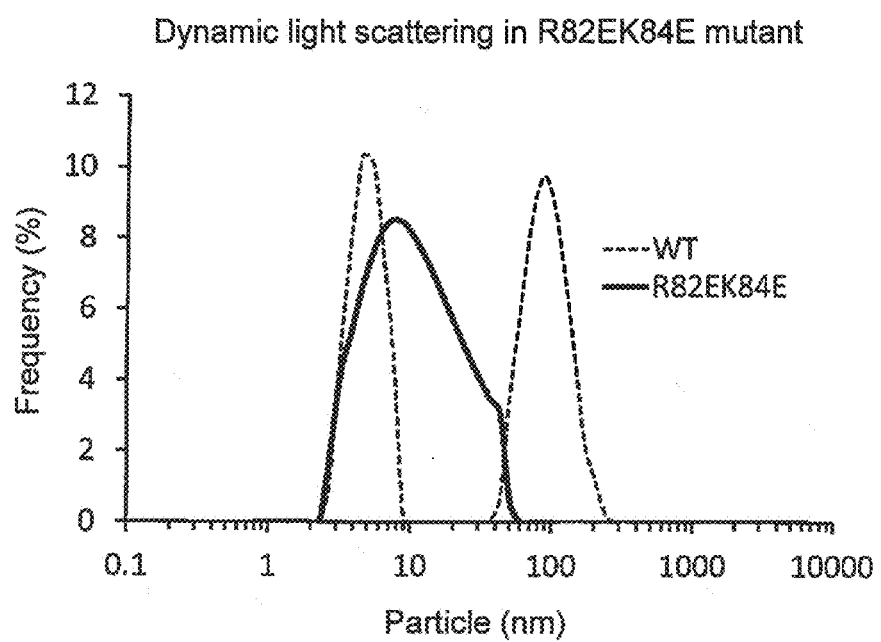
FIG. 6 is a graph showing measured particle diameters of wild-type UnaG protein and R82EK84E mutated UnaG protein in Example of the present invention.

Protein solutions (each 20 µL) of wild-type UnaG protein (10 mg/mL) and R82EK84E mutated UnaG protein (8.5 mg/mL) were each supplied to Microtrac particle size analyzer MT3000II (Nikkiso Co., Ltd.), and the particle diameters were measured by a dynamic light scattering. The aggregability was evaluated by plotting frequency against particle diameter. The results are shown in FIG. 6.

<Analysis of Fluorescent Properties of R82EK84E Mutant>

In order to analyze the fluorescent properties of R82EK84E mutant, the fluorescence spectrum, absorption spectrum, and quantum yield were measured. The measurement was performed by the same method as that described in the above-described paragraph 3. The fluorescence lifetime was measured with a small-sized fluorescence lifetime measurement system, Quantaurus-Tau (Hamamatsu Photonics K.K.) and was compared to that of wild-type UnaG protein. The results are shown in Table 3.

(Result)

TABLE 3

|  | Wild-type | R82EK84E mutant |
|---|---|---|
| Maximum excitation/fluorescence wavelength (nm) | 498/527 | 498/527 |
| Molar extinction coefficient ($M^{-1}$ $cm^{-1}$) | 56,992 | 50,870 |
| Quantum yield (%) | 51 | 61 |
| Fluorescence lifetime (τ1/ns) | 2.2 | 2.2 |

FIG. 6 is a graph showing measured particle diameters of wild-type UnaG protein and R82EK84E mutated UnaG protein. The horizontal axis indicates particle diameter (urn), and the vertical axis indicate frequency (%). As shown in FIG. 6, the wild-type showed two peaks of different particle diameter distribution ranges. The peak of a smaller-particle-diameter distribution range probably shows the monomer, and the peak of a larger-particle-diameter distribution range is probably of aggregate. In contrast, the R82EK84E mutant showed a single peak at the position overlapping the smaller-particle-diameter distribution range of the two peaks in the wild-type. That is, the R82EK84E mutant has improved dispersibility and is prevented from aggregating compared to the wild-type.

[7. Detection of Bilirubin in Human Serum]
(Material and Method)
<Binding of Apo UnaG Protein and Bilirubin by Titration>

An apo UnaG protein solution having an apo UnaG protein concentration of 5 nM was titrated with bilirubin to give a final concentration of bilirubin of 10 nM, and the fluorescence spectrum was measured with a fluorescence spectrophotometer. The fluorescence intensity at a maximum fluorescence wavelength of 527 nm of each of data was graphed using graph plotting software, Origin (OriginLab Corporation), and the dissociation constant was determined by curve-fitting using the following expression:

$$Y = [K_d + B_t + P_t - \{(K_d + B_t + P_t)^{1/2}\}]/(2 \times P_t)$$

where Y represents the degree of binding of bilirubin (fluorescence intensity); $K_d$ represents the dissociation constant; $B_t$ represents the concentration of bilirubin; and $P_t$ represents the concentration (5 nM) of apo UnaG protein.

<Detection of Unconjugated Bilirubin in Human Serum>

Experiments using human specimens were performed in accordance with "Regulations on research using human subjects" in Independent Administrative Institution RIKEN under permission.

Blood (5 mL) was collected in a vacuum sealed blood collection tube (Neo-Tube, NIPRO) from a vein of the arm using a needle of 23G (Terumo Corporation) and a 5-mL cylinder (Terumo Corporation). The collected blood was shielded from light and was left to stand at room temperature for 30 min and was then centrifuged at a rotation speed of 3,000 rpm for 20 min (KUBOTA K-80) to collect about 2.5 mL of serum. The collected serum was cooled with ice while being shielded from light and was promptly subjected to measurement of bilirubin.

Apo UnaG was added to the serum diluted with PBS by 200-fold so as to give a final concentration of 0.5 μM, and 200 μL of the mixture was added to each well of a 96-well microplate (black, non-binding, Greiner Bio-One). Measurement of fluorescence was started immediately after the addition of samples to the plate. The fluorescence intensity was measured at room temperature at every 10 min for 1 hr at a fluorescence wavelength of 527 nm (excitation wavelength: 497 nm) using EnSpire (trademark) multi-mode plate reader (PerkinElmer Co., Ltd.). Each serum was measured using three wells, and the serum not mixed with apo UnaG protein was also measured as background. The net fluorescence intensity was determined by subtracting the intensity level of the background from the intensity level of the serum mixed with apo UnaG protein. The results are shown in FIG. 7.

Figure 8:
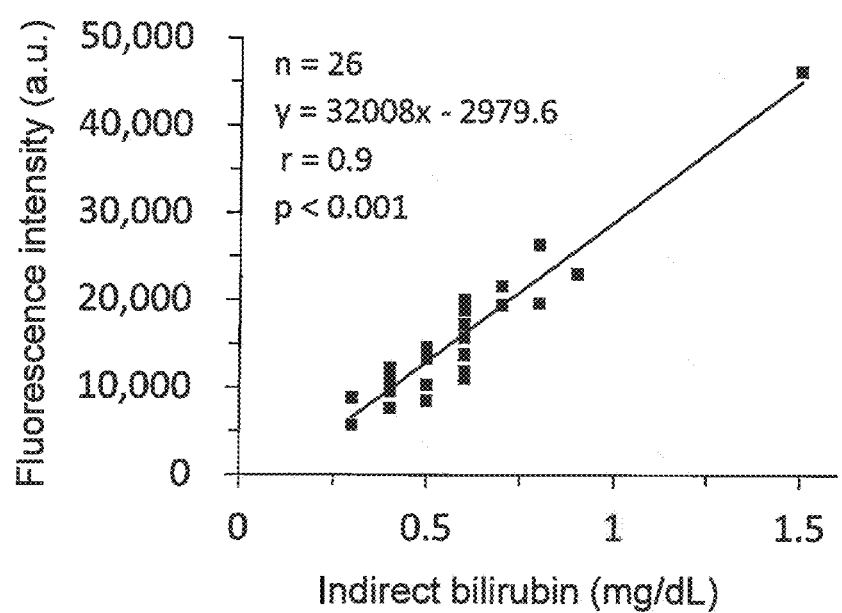

In addition, we asked LSI Medience Corporation to measure the total bilirubin level and direct bilirubin level in each serum by a biochemical test, an enzymatic method (Doumas, B. T., et al., Clin. Chem., 33, 1349-1353, 1987; Kurosaka, K. et al., Clin. Chim. Acta., 269, 125-436, 1998), and determined the indirect bilirubin value by a calculation method. The calculation method determines the indirect bilirubin level by measuring the total bilirubin level and the direct bilirubin level and subtracting the direct bilirubin level from the total bilirubin level. The correlation coefficient between the indirect bilirubin level and fluorescence intensity of UnaG in serum was determined. The results are shown in FIG. 8.

(Result)

Figure 7:
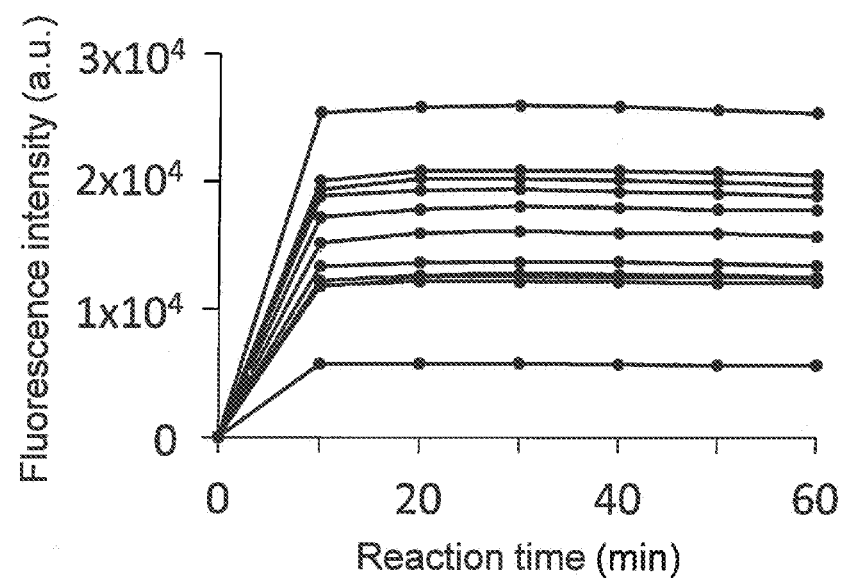
FIG. 7 is a graph showing fluorescence detection results (10 specimens) When apo UnaG (2 µM) was mixed with human serum (200-fold dilution) in Example of the present invention. The vertical axis indicates fluorescence intensity, and the horizontal axis indicates the time elapsed from the addition (0 min) of ape UnaG protein to serum.

FIG. 7 is a graph showing fluorescence detection results when UnaG is mixed into human serum. The vertical axis indicates the time elapsed from the addition (0 min) of apo UnaG protein to serum, and the horizontal axis indicates fluorescence intensity. The test results of 10 specimens are shown.

As shown in FIG. 7, even in 200-fold diluted serum, sufficient fluorescence intensity could be observed. It was thus suggested that bilirubin, can be measured even if the amount of serum is very small. Stable fluorescence is generated after about 10 min and further lasts for 1 hr or more. Accordingly, data can be obtained with high repeatability by measuring at an appropriate time after 10 min or more from the addition.

FIG. 8 is a graph showing a correlation between the amount of bilirubin and fluorescence intensity of UnaG The horizontal axis indicates the concentration of indirect bilirubin (unconjugated bilirubin) contained in serum, and the vertical axis indicates fluorescence intensity. It has been shown that there is a high correlation between the fluorescence intensity of UnaG protein and the concentration of indirect bilirubin in serum.

[8. Production of UnaG Mutant Having Low Bilirubin Binding Property]
(Material and Method)
<Random Mutagenesis>

Mutation was randomly introduced into wild-type UnaG by PCR using Diversify (registered trademark) PCR random mutagenesis kit (Clonetech). The DNA to be inserted into a vector was amplified by PCR using the wild-type UnaG as a template DNA and using sense (SEQ ID NO: 31) and antisense (SEQ ID NO: 32) primers. The amplified DNA fragment was ligated to the BamHI/EcoRI restriction enzyme sites of pRSETB-mCherry vector, which is *Escherichia coli* expression vector pRSETB including a mCherry sequence at the KpnI/BamHI restriction enzyme sites of the vector, and was then transformed into *Escherichia coli* strain JM109 (DE3) for cloning. The amino acid sequence and nucleotide sequence of mCherry are shown as SEQ ID NO: 33 and SEQ ID NO: 34, respectively.

<Screening (Colony Titration)>

Figure 9:
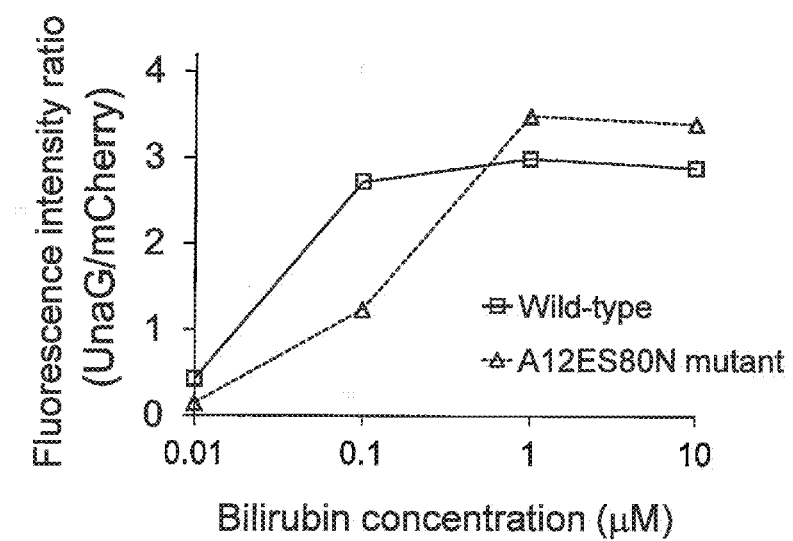
FIG. 9 is a graph showing a correlation between the amount of indirect bilirubin (unconjugated bilirubin) and fluorescence intensity of UnaG protein in Example of the present invention.

Colonies randomly picked up from the *Escherichia coli* colonies prepared by the above-described transformation were inoculated in 1 mL of an LB medium and were cultured at 17° C. overnight. After centrifugation at a rotation speed of 8,000 rpm for 1 min, the supernatant was removed. The collected bacterial cells were stirred with 400 μL of B-PER Protein Extraction Reagent (Thermo Scientific) for 5 min. After centrifugation at a rotation speed of 8,000 rpm at 4° C. for 3 min, the supernatant was collected. Each sample was dispensed into four wells of a 96-well microplate (FIA black plate, Greiner Bio-One) in an amount of 50 μL for each well. The final concentration of bilirubin in each sample was adjusted to 0.01, 0.1, 1.0, or 10 μM by adding 150 μL of a bilirubin solution. After incubation at room temperature for 20 min, the fluorescence intensities of the wild-type and mutant of UnaG were measured at a fluorescence wavelength of 527 nm with an excitation wavelength of 497 nm using EnSpire (registered trademark) multi-mode plate reader (PerkinElmer Co., Ltd.). The fluorescence intensity of mCherry was measured at a wavelength of 610 nm with an excitation wavelength of 580 nm. Fluorescence intensity ratios of UnaG protein to mCherry were determined and plotted. FIG. 9 shows the results of plotting of UnaG mutant protein of each clone showing low affinity to bilirubin compared to wild-type UnaG protein and maintaining a fluorescence intensity equivalent to that of the wild-type.

The clone showing low affinity to bilirubin compared to wild-type UnaG protein and maintaining a fluorescence intensity equivalent to that of the wild-type was replicated and was subjected to DNA sequence analysis using Applied Biosystems 3730xl DNA Analyzer (Applied Biosystems). The sequence was determined using gene analysis software, DNAdynamo (Blue Tractor Software Ltd.).
(Result)

The results of the sequence analysis demonstrate that the variant includes an amino acid Sequence having substitution of A at the 12th position of the wild-type to E and S at the 80th position of the wild-type to N (hereinafter, referred to A12ES80N mutant). The resulting amino acid sequence is shown as SEQ ID NO: 29.

FIG. 9 is a graph showing a correlation between the concentration of bilirubin and the fluorescence intensity ratio of wild-type UnaG protein or A12ES80N mutated UnaG protein to mCherry protein. The horizontal axis indicates the concentration of bilirubin, and the vertical axis indicates the fluorescence intensity ratio.

[9. Analysis of Mutant Having Low Affinity to Bilirubin, A12ES80N Mutant Protein]
<Expression of A12ES80N Mutant UnaG Protein (Apo Form) in *Escherichia Coli*>

A DNA fragment of A12ES80N mutant was ligated into BamHI and EcoRI restriction enzyme sites of pRSETB-FLAG vector, which was *Escherichia coli* expression vector pcRSETB including a FLAG tag sequence (SEQ ID NO: 26) at the KpnI/BamHI restriction enzyme sites, and was transformed into *Escherichia coli* strain JM109 (DE3) for subcloning.

The colony on the LB plate was inoculated in 50 mL of an LB liquid medium and was cultured at 17° C. for 3 days for inducing expression of UnaG. *Escherichia coli* cells were collected by centrifugation at 8,000 rpm for 3 min.

The bacterial cells were suspended in 5 mL of PBS, and 50 μL of lysozyme (4 mg/mL) was added thereto. The mixture was frozen with liquid nitrogen and was then thawed. This freeze and thaw process was repeated three times. After ultrasonication for 3 min, the supernatant of centrifugation at a rotation speed of 7,000 rpm at 4° C. for 20 min was collected to obtain a lysate. The lysate and 1 mL of Ni-NTA Agarose (QIAGEN) equilibrated with PBS were incubated at 4° C. for 1 hr to immobilize the His-FLAG-fused UnaG to the carrier. The carrier was rinsed with PBS containing 5 nM imidazole in a volume of 10 times or more the total volume of the carrier and then with PBS containing 10 mM imidazole in a volume of 15 times or more the total volume of the carrier. Subsequently, His-FLAG-UnaG mutant protein was eluted by adding each 500 μL of PBS containing 300 mM imidazole to the carrier, and the elution fraction was detected by a bradford method. The elution fraction was collected and was concentrated by ultrafiltration using Amicon Ultra-4 (Merck Millipore Corporation). In order to remove imidazole, the concentrated protein solution was added to a desalting column PD-10 (GE Healthcare) equilibrated with PBS. His-FLAG-UnaG mutant protein was eluted by adding each 500 μL of PBS, and the elution fraction was detected by a bradford method. The concentration of the purified His-FLAG-UnaG mutant protein was determined by the following computation expression based on the absorbance $A_{280}$. The purification was then confirmed by SDS-PAGE electrophoresis.

$$\varepsilon_M = Trp(2) \times 5500 + Tyr(7) \times 1490 + Cystine(0) \times 125 = 21430(A_{280}/\text{mol/cm}); \text{ and}$$

$$\text{Protein concentration} = A_{280}/\varepsilon_M = A_{280}/21430(\text{mol}/\text{dm}^3).$$

After purification, the holo form was prepared by reconstructing with bilirubin. The holo form was prepared by the same method as that described in paragraph 2-2. above.
<Analysis of Fluorescent Properties of A12ES80N Mutant>

Figure 10:
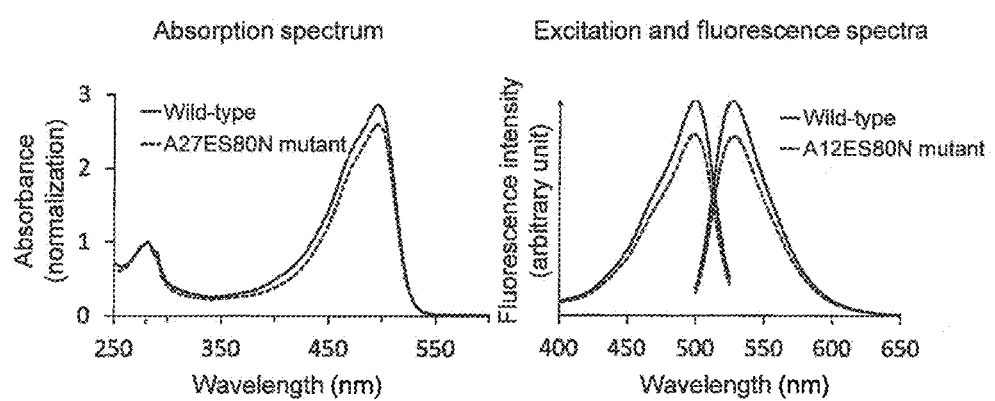
FIG. 10 includes graphs showing the fluorescent properties of A12ES80N mutated UnaG protein in Example of the present invention. The graph in the left shows an absorption spectrum of A12ES80N mutated UnaG protein, where the horizontal axis indicates the wavelength of absorbed light, and the vertical axis indicates absorbance. The graph in the right shows an excitation spectrum and the fluorescence spectrum of A12ES80N mutated UnaG protein, where the horizontal axis indicates wavelengths of excitation light and fluorescence, and the vertical axis indicates fluorescence intensity.

The fluorescence spectrum, absorption spectrum, and quantum yield (excitation wavelength: 470 nm) were measured for analyzing the fluorescent properties of holo A12ES80N mutant protein. The measurement was performed by the same method as that described in paragraph 3, above. The fluorescent properties were compared to those of wild-type UnaG protein. The results are shown in FIG. 10 and Table 4.
(Result)

TABLE 4

| | Wild-type | A12ES80N mutant |
|---|---|---|
| Maximum excitation/fluorescence wavelength (nm) | 499/527 | 499/527 |
| Molar extinction coefficient ($M^{-1}$ $cm^{-1}$) | 52,687 | 56,210 |
| Quantum yield (%) | 53.2 | 46.8 |

FIG. 10 includes graphs showing the fluorescent properties of A12ES80N mutated UnaG protein. The graph in the left shows an absorption spectrum of A12ES80N mutated UnaG protein, where the horizontal axis indicates the wavelength of absorbed light, and the vertical axis indicates absorbance. The graph in the right shows an excitation spectrum and the fluorescence spectrum of A12ES80N mutated UnaG protein, where the horizontal axis indicates wavelengths of excitation light and fluorescence, and the vertical axis indicates fluorescence intensity.

[9. Evaluation of Bilirubin Binding Performance of A12ES80N Mutant]
(Material and Method)
<Measurement of Dissociation Constant>

Apo A12ES80N mutant protein was titrated with bilirubin, and the fluorescence intensity was measured with a spectrophotofluorometer F-2500 (Hitachi High-Technologies Corporation). The results were plotted. Data analysis and fitting with graph plotting software Origin (OriginLab Corporation) were performed to determine the dissociation constant (Kd). The titration with bilirubin and the measurement of dissociation constant were performed by the same methods as those described in paragraph 7. The results are shown in FIG. 11.

(Result)

Figure 11:
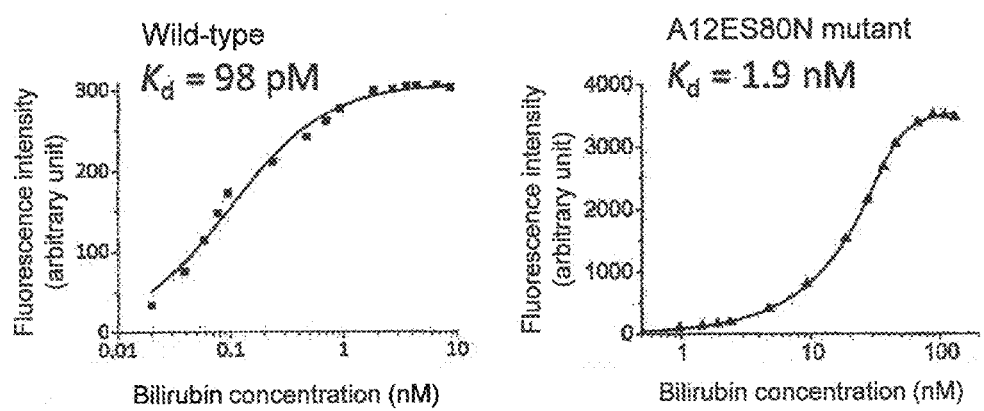
FIG. 11 includes graphs showing correlations between the amount of bilirubin and fluorescence intensity of wild-type UnaG protein (left) or A12ES80N mutated UnaG protein (right) in Example of the present invention.

FIG. 11 includes graphs showing correlations between the amount of bilirubin and fluorescence intensity of wild-type UnaG protein (left) or A12ES80N mutated UnaG protein (right). The results of curve fitting demonstrate that A12ES80N mutant binds to bilirubin with a dissociation constant $K_d$ of 1.9 nM, whereas the Mid-type UnaG does with a dissociation constant $K_d$ of 98 pM.

The present invention is not limited to the above-described embodiments and Examples and can be variously modified within the scope of the claims, and embodiments brought by appropriately combining technical means respectively disclosed in different embodiments also fall in the technical range of the present invention. Furthermore, all documents cited in the specification are incorporated by reference herein in their entirety.

INDUSTRIAL APPLICABILITY

The present invention provides a protein derived from Japanese eel and having novel fluorescent properties. The invention can provide a novel method for detecting bilirubin using the polypeptide of the present invention as a biomarker.

The invention claimed is:

1. A method for detecting bilirubin in a subject, the method comprising:
contacting a sample from the subject with a polypeptide, wherein the polypeptide has fluorescent activity upon binding to bilirubin; and
detecting fluorescence emitted by the polypeptide after the contacting step,
wherein the presence of fluorescence emission detects bilirubin in the subject, and
wherein the polypeptide is selected from the group consisting of:
(1) a polypeptide comprising the amino acid sequence of SEQ ID NO: 1;
(2) a polypeptide comprising an amino acid sequence that has at least 95% sequence identity to the amino acid sequence of SEQ ID NO: 1;
(3) a polypeptide comprising the amino acid sequence of SEQ ID NO: 1, except for an amino substitution selected from the group consisting of A12E, S80N, R82E, K84E, and combinations thereof in the amino acid sequence of SEQ ID NO: 1; and
(4) a polypeptide comprising the amino acid sequence of SEQ ID NO: 5 or SEQ ID NO: 29.

2. The method according to claim 1, wherein the sample is derived from blood or urine collected from the subject.

3. The method according to claim 1, further comprising:
a testing step of inspecting the presence or absence of a predisposing factor or onset of liver disease or hemolytic disease based on a detection result in the detecting step.

4. The method according to claim 1, wherein the polypeptide is a fusion polypeptide.

5. The method according to claim 1, wherein the polypeptide comprises the amino acid sequence of SEQ ID NO: 1, SEQ ID NO: 5, SEQ ID NO: 29, or SEQ ID NO: 1 except for an amino acid substitution selected from the group consisting of A12E, S80N, R82E K84E and combinations thereof in the amino acid sequence of SEQ ID NO: 1.

6. The method according to claim 1, wherein the subject is a human, or is a nonhuman animal.

7. The method according to claim 1, where the polypeptide comprises the amino acid sequence of SEQ ID NO: 1.

8. The method according to claim 1, where the polypeptide comprises an amino acid sequence that has at least 95% sequence identity to the amino acid sequence of SEQ ID NO: 1.

9. The method according to claim 1, wherein the polypeptide comprises the amino acid sequence of SEQ ID NO: 1, except for an amino acid substitution selected from the group consisting of A12E, S80N, R82E, K84E, and combinations thereof in the amino acid sequence of SEQ ID NO: 1.

10. The method according to claim 1, wherein the polypeptide comprises the amino acid sequence of SEQ ID NO: 5 or SEQ ID NO: 29.

* * * * *

SEQUENCE LISTING

```
<160> NUMBER OF SEQ ID NOS: 34

<210> SEQ ID NO 1
<211> LENGTH: 139
<212> TYPE: PRT
<213> ORGANISM: Anguilla japonica

<400> SEQUENCE: 1

Met Val Glu Lys Phe Val Gly Thr Trp Lys Ile Ala Asp Ser His Asn
1               5                   10                  15

Phe Gly Glu Tyr Leu Lys Ala Ile Gly Ala Pro Lys Glu Leu Ser Asp
                20                  25                  30

Gly Gly Asp Ala Thr Thr Pro Thr Leu Tyr Ile Ser Gln Lys Asp Gly
            35                  40                  45

Asp Lys Met Thr Val Lys Ile Glu Asn Gly Pro Pro Thr Phe Leu Asp
        50                  55                  60

Thr Gln Val Lys Phe Lys Leu Gly Glu Glu Phe Asp Glu Phe Pro Ser
65                  70                  75                  80

Asp Arg Arg Lys Gly Val Lys Ser Val Val Asn Leu Val Gly Glu Lys
                85                  90                  95

Leu Val Tyr Val Gln Lys Trp Asp Gly Lys Glu Thr Thr Tyr Val Arg
                100                 105                 110

Glu Ile Lys Asp Gly Lys Leu Val Val Thr Leu Thr Met Gly Asp Val
            115                 120                 125

Val Ala Val Arg Ser Tyr Arg Arg Ala Thr Glu
        130                 135

<210> SEQ ID NO 2
<211> LENGTH: 420
<212> TYPE: DNA
<213> ORGANISM: Anguilla japonica

<400> SEQUENCE: 2
atggtcgaga aatttgttgg cacctggaag atcgcagaca gccataattt tggtgaatac      60
ctgaaagcta tcggagcccc aaaggaatta agcgatggtg gggatgccac gacgccgaca     120
ttgtacatct cccagaagga cggagacaaa atgacagtga aaatagagaa tggacctcct     180
acgttccttg acactcaagt aaagttcaaa ttaggggagg agttcgacga atttccttct     240
gatcgaagaa aaggcgtaaa atctgtcgtg aacttggtgg gagagaagct ggtgtacgta     300
caaaagtggg acggcaagga gacgacgtat gtccgagaga taaggacgg taaactggtc      360 gtgacactta cgatgggaga cgtcgtggct gtgcgcagct accggagggc gacggaatga     420

<210> SEQ ID NO 3
```

```
<211> LENGTH: 139
<212> TYPE: PRT
<213> ORGANISM: Anguilla japonica

<400> SEQUENCE: 3

Met Val Glu Lys Phe Val Gly Thr Trp Lys Ile Ala Asp Ser His Asn
1               5                   10                  15

Phe Gly Glu Tyr Leu Lys Ala Ile Gly Ala Pro Lys Glu Leu Ser Asp
            20                  25                  30

Gly Gly Asp Ala Thr Thr Pro Thr Leu Tyr Ile Ser Gln Lys Asp Gly
        35                  40                  45

Asp Lys Met Arg Val Lys Ile Glu Asn Gly Pro Pro Thr Phe Leu Asp
    50                  55                  60

Thr Glu Val Lys Phe Lys Leu Gly Glu Glu Phe Asp Glu Phe Pro Ser
65                  70                  75                  80

Asp Arg Arg Lys Gly Val Lys Ser Val Val Asn Leu Val Gly Glu Lys
                85                  90                  95

Leu Val Tyr Val Gln Lys Trp Asp Gly Lys Glu Thr Tyr Val Arg
            100                 105                 110

Glu Ile Lys Asp Gly Lys Leu Val Val Thr Leu Thr Met Gly Asp Val
            115                 120                 125

Val Ala Val Arg Ser Tyr Arg Arg Ala Thr Glu
        130                 135

<210> SEQ ID NO 4
<211> LENGTH: 420
<212> TYPE: DNA
<213> ORGANISM: Anguilla japonica

<400> SEQUENCE: 4
atggtcgaga aatttgttgg cacctggaag atcgcagaca gccataattt tggtgaatac      60
ctgaaagcta tcggagcccc aaaggaatta agcgatggtg gggatgccac gacgccgaca     120
ttgtacatct cccagaagga cggagacaaa atgagagtga aaatagagaa tggacctcct     180
acgttccttg acactgaagt aaagttcaaa ttaggggagg agttcgacga atttccttct     240
gatcgaagaa aaggcgtaaa atctgtcgtg aacttggtgg gagagaagct ggtgtacgta     300
caaaagtggg acggcaagga gacgacgtat gtccgagaga taaggacgg  taaactggtc     360 gtgacactta cgatgggaga cgtcgtggct gtgcgcagct accggagggc gacggaatga     420

<210> SEQ ID NO 5
<211> LENGTH: 139
<212> TYPE: PRT
<213> ORGANISM: Anguilla japonica

<400> SEQUENCE: 5

Met Val Glu Lys Phe Val Gly Thr Trp Lys Ile Ala Asp Ser His Asn
1               5                   10                  15

Phe Gly Glu Tyr Leu Lys Ala Ile Gly Ala Pro Lys Glu Leu Ser Asp
            20                  25                  30

Gly Gly Asp Ala Thr Thr Pro Thr Leu Tyr Ile Ser Gln Lys Asp Gly
        35                  40                  45

Asp Lys Met Thr Val Lys Ile Glu Asn Gly Pro Pro Thr Phe Leu Asp
    50                  55                  60

Thr Gln Val Lys Phe Lys Leu Gly Glu Glu Phe Asp Glu Phe Pro Ser
65                  70                  75                  80

Asp Glu Arg Glu Gly Val Lys Ser Val Val Asn Leu Val Gly Glu Lys
```

85                  90                  95
Leu Val Tyr Val Gln Lys Trp Asp Gly Lys Glu Thr Thr Tyr Val Arg
            100                 105                 110

Glu Ile Lys Asp Gly Lys Leu Val Val Thr Leu Thr Met Gly Asp Val
        115                 120                 125

Val Ala Val Arg Ser Tyr Arg Arg Ala Thr Glu
    130                 135

<210> SEQ ID NO 6
<211> LENGTH: 420
<212> TYPE: DNA
<213> ORGANISM: Anguilla japonica

<400> SEQUENCE: 6
atggtcgaga aatttgttgg cacctggaag atcgcagaca gccataattt tggtgaatac     60
ctgaaagcta tcggagcccc aaaggaatta agcgatggtg gggatgccac gacgccgaca    120
ttgtacatct cccagaagga cggagacaaa atgacagtga aaatagagaa tggacctcct    180
acgttccttg acactcaagt aaagttcaaa ttaggggagg agttcgacga atttccttct    240
gatgaaagag aagggtaaa atctgtcgtg aacttggtgg gagagaagct ggtgtacgta    300
caaaagtggg acggcaagga gacgacgtat gtccgagaga taaggacgg taaactggtc    360 gtgacactta cgatgggaga cgtcgtggct gtgcgcagct accggagggc gacggaatga    420

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 7
gcnathggng cnccnaar                                                   18

<210> SEQ ID NO 8
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)

```
<223> OTHER INFORMATION: n is a, c, g, or t

<400> SEQUENCE: 8
ytngtntayg tncaraar                                          18

<210> SEQ ID NO 9
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t

<400> SEQUENCE: 9
tgggayggna argar                                             15

<210> SEQ ID NO 10
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 10
aargaracna cntay                                             15

<210> SEQ ID NO 11
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 11
garytnwsng ayggnggnga y                                      21

<210> SEQ ID NO 12
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 12
gayggnggng aygcngcn                                                18

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 13
athgcngayw sncayaaytt y                                            21

<210> SEQ ID NO 14
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t

<400> SEQUENCE: 14
cayaayttyg gngartay                                                18

<210> SEQ ID NO 15
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

```
<400> SEQUENCE: 15
garaayggnc cnccnacntt y                                             21

<210> SEQ ID NO 16
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 16
acnttyytng ayacngar                                                 18

<210> SEQ ID NO 17
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: n is inocine
<220> FEATURE:
<221> NAME/KEY: misc_feature
<222> LOCATION: (29)..(30)
<223> OTHER INFORMATION: n is inocine
<220> FEATURE:
<221> NAME/KEY: misc_feature
<222> LOCATION: (34)..(35)
<223> OTHER INFORMATION: n is inocine

<400> SEQUENCE: 17
ggccacgcgt cgactagtac gggnngggnn gggnng                             36

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
gccctccggt agctgcgcac agcc                                          24

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
gcgcacagcc acgacgtctc cc                                            22

<210> SEQ ID NO 20
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 20
gtacgtacac cagcttctct cccacc                                          26

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
ctctcccacc aagttcacca ca                                              22

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
gctttgcgag catctacttt ttattctcc                                       29

<210> SEQ ID NO 23
<211> LENGTH: 44
<212> TYPE: DNA
<213> ORGANISM: Artificial Sequence
<220> FEATURE:
<223> OTHER INFORMATION: Synthetic

<400> SEQUENCE: 23
gactagttct agatcgcgag cggccgccct tttttttttt tttt                      44

<210> SEQ ID NO 24
<211> LENGTH: 50
<212> TYPE: DNA
<213> ORGANISM: Artificial Sequence
<220> FEATURE:
<223> OTHER INFORMATION: Synthetic

<400> SEQUENCE: 24
cgggatccgg tggttctggt atggtcgaga aatttgttgg cacctggaag                50

<210> SEQ ID NO 25
<211> LENGTH: 43
<212> TYPE: DNA
<213> ORGANISM: Artificial Sequence
<220> FEATURE:
<223> OTHER INFORMATION: Synthetic

<400> SEQUENCE: 25
cgcgaattct cattccgtcg ccctccggta gctgcgcaca gcc                       43

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
```

-continued atggattaca aggatgacga cgataag                                    27

<210> SEQ ID NO 27
<211> LENGTH: 39
<212> TYPE: DNA
<213> ORGANISM: Artificial Sequence
<220> FEATURE:
<223> OTHER INFORMATION: Synthetic

<400> SEQUENCE: 27
gaatttcctt ctgatgaaag agaagggta aaatctgtc                        39

<210> SEQ ID NO 28
<211> LENGTH: 39
<212> TYPE: DNA
<213> ORGANISM: Artificial Sequence
<220> FEATURE:
<223> OTHER INFORMATION: Synthetic

<400> SEQUENCE: 28
gacagatttt acgccttctc tttcatcaga aggaaattc                       39

<210> SEQ ID NO 29
<211> LENGTH: 139
<212> TYPE: PRT
<213> ORGANISM: Anguilla japonica

<400> SEQUENCE: 29

Met Val Glu Lys Phe Val Gly Thr Trp Lys Ile Glu Asp Ser His Asn
1               5                   10                  15

Phe Gly Glu Tyr Leu Lys Ala Ile Gly Ala Pro Lys Glu Leu Ser Asp
            20                  25                  30

Gly Gly Asp Ala Thr Thr Pro Thr Leu Tyr Ile Ser Gln Lys Asp Gly
        35                  40                  45

Asp Lys Met Thr Val Lys Ile Glu Asn Gly Pro Pro Thr Phe Leu Asp
    50                  55                  60

Thr Gln Val Lys Phe Lys Leu Gly Glu Glu Phe Asp Glu Phe Pro Asn
65                  70                  75                  80

Asp Arg Arg Lys Gly Val Lys Ser Val Val Asn Leu Val Gly Glu Lys
                85                  90                  95

Leu Val Tyr Val Gln Lys Trp Asp Gly Lys Glu Thr Thr Tyr Val Arg
            100                 105                 110

Glu Ile Lys Asp Gly Lys Leu Val Val Thr Leu Thr Met Gly Asp Val
        115                 120                 125

Val Ala Val Arg Ser Tyr Arg Arg Ala Thr Glu
    130                 135

<210> SEQ ID NO 30
<211> LENGTH: 420
<212> TYPE: DNA
<213> ORGANISM: Anguilla japonica

<400> SEQUENCE: 30
atggtcgaga aatttgttgg cacctggaag atcgaagaca gccataattt tggtgaatac    60
ctgaaagcta tcggagcccc aaaggaatta agcgatggtg gggatgccac gacgccgaca   120
ttgtacatct cccagaagga cggagacaaa atgacagtga aaatagagaa tggacctcct   180
acgttccttg acactcaagt aaagttcaaa ttaggggagg agttcgacga atttcctaac   240
gatcgaagaa aaggcgtaaa atctgtcgtg aacttggtgg gagagaagct ggtgtacgta   300

```
caaaagtggg acggcaagga gacgacgtat gtccgagaga taaaggacgg taaactggtc    360
gtgacactta cgatgggaga cgtcgtggct gtgcgcagct accggagggc gacggaatga    420
```

<210> SEQ ID NO 31
<211> LENGTH: 50
<212> TYPE: DNA
<213> ORGANISM: Artificial Sequence
<220> FEATURE:
<223> OTHER INFORMATION: sense primer

<400> SEQUENCE: 31

```
cgggatccgg tggttctggt atggtcgaga aatttgttgg cacctggaag               50
```

<210> SEQ ID NO 32
<211> LENGTH: 43
<212> TYPE: DNA
<213> ORGANISM: Artificial Sequence
<220> FEATURE:
<223> OTHER INFORMATION: Antisense primer

<400> SEQUENCE: 32

```
cgcgaattct cattccgtcg ccctccggta gctgcgcaca gcc                      43
```

<210> SEQ ID NO 33
<211> LENGTH: 236
<212> TYPE: PRT
<213> ORGANISM: Discosoma striata

<400> SEQUENCE: 33

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys

<210> SEQ ID NO 34
<211> LENGTH: 708
<212> TYPE: DNA
<213> ORGANISM: Discosoma striata

<400> SEQUENCE: 34

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg cccgctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tcccctccga cggcccccgta    420
atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaag              708
```